(12) United States Patent
Adolphson et al.

(10) Patent No.: US 11,986,168 B2
(45) Date of Patent: May 21, 2024

(54) DEVICES, SYSTEMS AND METHODS FOR SURFACE SAMPLING

(71) Applicant: InnovaPrep LLC, Drexel, MO (US)

(72) Inventors: Alec D. Adolphson, Raymore, MO (US); Ann K. Packingham, Cleveland, MO (US); Andrew E. Page, Smithton, MO (US); David S. Alburty, Drexel, MO (US); Zachary A. Packingham, Drexel, MO (US); John D. Birkenholz, Kansas City, MO (US); Michael F. Fischer, Lee's Summit, MO (US)

(73) Assignee: INNOVAPREP, LLC, Drexel, MO (US)

( * ) Notice: Subject to any disclaimer, the term of this patent is extended or adjusted under 35 U.S.C. 154(b) by 461 days.

(21) Appl. No.: 17/103,912

(22) Filed: Nov. 24, 2020

(65) Prior Publication Data

US 2021/0077080 A1 Mar. 18, 2021

Related U.S. Application Data

(63) Continuation of application No. 15/132,046, filed on Apr. 18, 2016, now Pat. No. 10,842,470.

(60) Provisional application No. 62/149,142, filed on Apr. 17, 2015.

(51) Int. Cl.
*A61B 10/02* (2006.01)
*A61B 10/00* (2006.01)
*B01L 3/00* (2006.01)
*G01N 1/02* (2006.01)

(52) U.S. Cl.
CPC .......... *A61B 10/02* (2013.01); *A61B 10/0096* (2013.01); *A61B 2010/0216* (2013.01); *B01L 3/5029* (2013.01); *G01N 2001/028* (2013.01)

(58) Field of Classification Search
CPC . A61B 10/02; A61B 10/0096; A61B 10/0045; A61B 2010/0216; B01L 3/5029; G01N 2001/028
See application file for complete search history.

(56) References Cited

U.S. PATENT DOCUMENTS

2010/0313686 A1* 12/2010 Page ................ G01N 1/02
73/863.22

FOREIGN PATENT DOCUMENTS

WO WO-2007016618 A1 * 2/2007 ......... A61B 10/0045

* cited by examiner

*Primary Examiner* — Devin B Henson
(74) *Attorney, Agent, or Firm* — MOAZZAM & ASSOCIATES, LLC

(57) ABSTRACT

Devices, systems and methods are disclosed which relate to using wet foam elution for removal of particles from swabs and wipes. This allow users to capture particles from surfaces and recover them by elution into small sample volumes for subsequent detection for human clinical, veterinary, food safety, pharmaceutical, outbreak investigations, forensics, biodefense and bioterrorism response, environmental monitoring, and other applications where collection of samples from surfaces and humans or animals is required. More specifically, the swabs or wipes are used to collect samples in the standard ways that commercially available swabs and wipes are in use today; from, for instance, food preparation surfaces in food plants, from production equipment in pharmaceutical facilities, for collection of dry powders during bioterrorism event response, and for collection of clinical samples such as nasal, throat, nasopharyngeal, and wounds.

14 Claims, 32 Drawing Sheets

DEVICES, SYSTEMS AND METHODS FOR SURFACE SAMPLING

This U.S. patent application is a continuation of Ser. No. 15/132,046, filed Apr. 18, 2016, now U.S. Pat. No. 10,842,470; which claims priority to U.S. Provisional Patent Application Ser. No. 62/149,142, filed on Apr. 17, 2015, the contents of which are hereby incorporated by reference herein in their entirety into this disclosure.

TECHNICAL FIELD

The present subject disclosure relates generally to the fields of human clinical, veterinary, food safety, pharmaceutical, outbreak investigations, forensics, biodefense and bioterrorism response, environmental monitoring, and other applications where collection of samples from surfaces and humans or animals is required. Swab and wipe sampling are routinely used in these and other fields to collect surface samples, human clinical, animal clinical and other sample types. More specifically, the present subject disclosure comprises systems, devices and methods for recovery of samples from swabs and wipes using a wet foam elution process.

BACKGROUND OF THE SUBJECT DISCLOSURE

A wide range of existing, and developing, rapid analysis platforms are potentially useful technologies for detection and identification needs. Detection and identification may key on whole organisms, nucleic acids, or proteins. Culture based analysis, antibiotic susceptibility testing, and functional assays all require live organism samples. Common nucleic acid techniques include qPCR, UHTS, and hybridization arrays. ELISA and other immunoassay techniques, mass spectrometry, chromatography techniques, and other techniques may be used for protein analysis. There are significant reasons in some cases to choose one of these techniques over the other or in some cases to analyze with more than one technique. The various systems and methods are powerful techniques for rapidly detecting and identifying pathogens and other microorganisms and biological particles, but they require good techniques and devices for efficiently delivering high-quality samples, and contained target organism in a small sample volume.

Swabs and wipes are routinely used as tools for collection of biological and non-biological materials from environmental and clinical samples. Samples are collected by swabbing or wiping an appropriate surface. The sample must then be recovered from the collection tool into a liquid buffer or in some cases directly onto a culture plate for biological samples. A number of methods exist for recovery of samples from swabs and wipes, but these methods are inefficient and often recover the samples into relatively large liquid volumes. Poor recoveries and large sample volumes result in samples that are often too dilute to allow for rapid detection. Further, it is desirable to be able to perform sample recovery in a field setting with minimal equipment and minimal user steps, but conventional methods frequently require a significant number of steps and a laboratory setting where vortexers, centrifuges, or other AC powered laboratory equipment are available.

SUMMARY OF THE SUBJECT DISCLOSURE

Novel, rapid and efficient swab and wipe elution systems, devices and methods are disclosed that allow users to capture and elute swab and wipe samples for human clinical, veterinary, food safety, pharmaceutical, outbreak investigations, forensics, biodefense and bioterrorism response, environmental monitoring, and other applications where collection of samples from surfaces and humans or animals is required. More specifically, the swabs and wipes are used to collect samples in the standard ways that are used today; from, for instance, food preparation surfaces in food plants, from production equipment in pharmaceutical facilities, for collection of dry powders, dry spill residues, or liquid spills during bioterrorism event response, and for collection of human and animal clinical samples such as nasal, throat, nasopharyngeal, and wounds.

After sample collection, various elution techniques may be used to elute target materials from swabs, including, for example, (1) elution down the lumen of the hollow shaft of a swab with the foam traveling from the inside to the outside of the swab and (2) enclosure of the swab in an elution chamber with the foam traveling across the outside surface of the swab head. Performing the elution in either of these two ways allows for the elution to be quickly and efficiently performed while using elution volumes significantly smaller than used in the traditional swab elution methods.

The present subject disclosure presents swab collection and elution devices that improve work flow for field and laboratory collection and elution of swab samples. In the case of hollow shaft swabs, the user pushes the swab onto the swab collection/elution instrument, and the swab can then be used in a dry state, or pre-wetted using the onboard wet foam. The present system provides a convenient tool for securely holding the swab during sample collection. After sample collection, the swab head is held inside an appropriate sample container and an elution button or lever is actuated, releasing elution foam through the swab head and into the sample container. The swab can then be automatically ejected into a waste container.

In another disclosed technique, a swab with or without a hollow shaft is used to collect a sample in the conventional way, and then the user inserts the swab head into the elution cartridge. The cartridge either seals around the swab shaft or the shaft is broken at a pre-scored line or an integral cutter is used to cut off the shaft and the cartridge seals the opening where the shaft previously was. The cartridge is then inserted into an elution system or an elution dispenser is pushed onto the cartridge and wet foam is dispensed into the hollow shaft or across the outside surface of the swab head. The foam elutes the collected target materials and is deposited into a sample reservoir within the cartridge. The collected sample can then be manually removed with a syringe or pipette device or automatically drawn from the reservoir into an assay portion of the cartridge or into a separate assay cartridge.

In addition to swabs, surface wipes and blotting devices are used for a variety of environmental surface and clinical specimen collections. Using similar wet foam elution processes to those described for swabs, these devices can also be eluted.

Swabs and wipes come in a variety of sizes, shapes and materials. The wet foam elution process described in Applicant's prior and co-pending patents and patent applications provide for an efficient technique for eluting particles from membrane filters, depth filters and similar fibrous and sponge-type materials that can also be used for collection from surfaces and clinical specimens. The following Applicant patents and pending applications are incorporated by reference herein in their entirety into this disclosure and disclose various elution methodologies, but none present the novel techniques of sample collection by swab or wipe as disclosed in the present subject matter: U.S. Pat. Nos. 8,110,112; 8,584,535 ("Applicant's Concentrating Pipette Instrument"); U.S. Pat. Nos. 8,584,536; 8,677,839; 8,677,840; 8,726,744; 8,758,623; U.S. patent application Ser. No. 14/058,193; U.S. patent application Ser. No. 14/191,205; U.S. patent application Ser. No. 14/313,618.

BRIEF DESCRIPTION OF THE DRAWINGS

The accompanying drawings, which are incorporated in and constitute a part of this specification, illustrate embodiments of the subject disclosure and technical data supporting those embodiments, and together with the written description, serve to explain certain principles of the subject disclosure.

DETAILED DESCRIPTION OF THE SUBJECT DISCLOSURE

Figure 1:
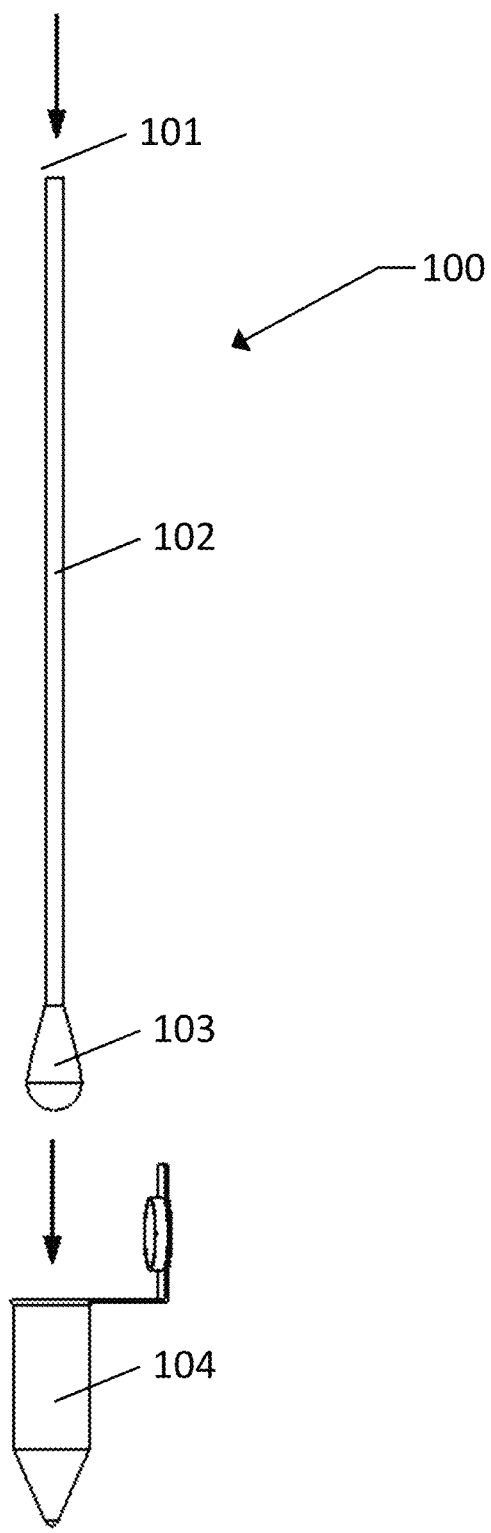
FIG. 1 shows the direction of wet foam elution flow down the hollow shaft and out through the swab head of a hollow-shaft swab, according to an exemplary embodiment of the present subject disclosure.

The following detailed description references specific embodiments of the subject disclosure and accompanying figures, including the respective best modes for carrying out each embodiment. It shall be understood that these illustrations are by way of example and not by way of limitation.

A detailed description of the disclosed swab and wipe elution techniques is provided below including a detailed description of the wet foam elution method and drawings of the disclosed devices.

Wet Foam Elution

Wet foam elution is a novel method for recovery of particles from filters, swabs, wipes and other surfaces. High-quality foam is produced by rapidly dispensing an elution solution containing a surfactant or other foaming agent from a high-pressure liquid-soluble gas atmosphere through a capillary, or other means of agitation, and into an expansion zone. The foam is then swept or across the material or surface to be extracted or eluted. Surfactants including Tween 20, Tween 80, Triton X-100, sodium dodecyl sulfate, and other ionic, nonionic, cationic and zwitterionic surfactants or proteins may be used as foaming agents. A range of other buffers may be added to maintain the elution fluid pH in a specific range or to supplement the fluid in other ways, such as maintain a specific ionic strength. Carbon dioxide and nitrous oxide are highly soluble in water under pressure and therefor work well as expansion gases. Other gases, such as nitrogen, may also be used alone or in combination with other gases to provide desired characteristics to the elution foam.

Foam has unique properties that make it a superior method for elution of particles from various materials and surfaces. Elution with aqueous foam has significant advantages over elution with standard aqueous solutions. Possibly the most important aspect of using foam for elution is the advantage gained by expanding the fluid to many times its original volume. Because most of the fluid simply goes toward filling the void volume of the inside of the swab or around the surface, rather than performing the actual elution at the surface, it is difficult to efficiently elute particles while keeping the elution volume small—and keeping the volume small is critical to keeping the target concentration in the eluted sample high. During wet foam elution, the liquid is expanded five or more times its original volume.

Foams are frequently used during tertiary extraction for enhanced oil recovery. Due to the high viscosity of foams, they exhibit reduced channeling thereby sweeping more oil out of porous media. This same characteristic makes foam ideal for extraction from complex materials and surfaces. One application that the ability of wet foam elution to improve elution efficiencies has been proven is in the use of hollow fiber membrane filter concentration modules for concentration of bacteria and viruses. It is well known that channeling or non-uniform flow distribution takes place in hollow fiber membrane filter modules that contain multiple fibers. Channeling is dependent on inlet manifold design, Reynolds number, pressure drop and other issues such as irregularity in fiber diameter. In short, channeling is difficult to control and is almost certainly at play during recovery of organisms from multiple fiber concentration units with aqueous extraction fluids.

Several research teams have recently studied this subject and determined that uniform foams in a capillary exhibit plug flow and self-lubricate with a very narrow lubricating layer thickness on the order of 10 μm or less. The foam moves as a rigid body lubricated by water generated by breaking foam at the wall. Because core flow is absent and the lubricating layer is thin, the foam is able to act with high shear in the fiber surface boundary layer to sweep away the captured particles. Furthermore, energy created by breaking bubbles may enhance particle removal from the hollow fiber surface and other surfaces or materials. The majority of the carbon dioxide bubbles in the wet foam burst soon after release into a lower pressure environment (e.g., atmospheric or near atmospheric), returning the foam to a liquid and allowing for transfer to the identifier as an aqueous sample. Most of the foam returns to a free liquid within two seconds.

Swab Collection/Elution

This disclosure presents various methods of wet foam elution of swabs. Two of the examples presented include (A) flow down the lumen of a hollow shaft swab and out through the swab head material, and (B) flow of foam across the swab head.

FIG. 1 shows the direction of flow during elution of a hollow shaft swab. Following collection of a sample with the hollow shaft swab 100, wet foam is introduced into the opening 101 of a hollow shaft 102. Following release, the wet foam travels down the lumen of the hollow shaft 102 and is pushed out through the swab head 103 and into a sample container 104. In the process particles that were earlier collected onto the swab head surface are now recovered into a small volume of foam, which breaks down into a small liquid sample. Various types of swabs may be used in this technique, including a standard hollow shaft swab, such as Puritan Medical's Standard 6" Polyester Swab with plastic handle (part #806-PD).

Figure 2:
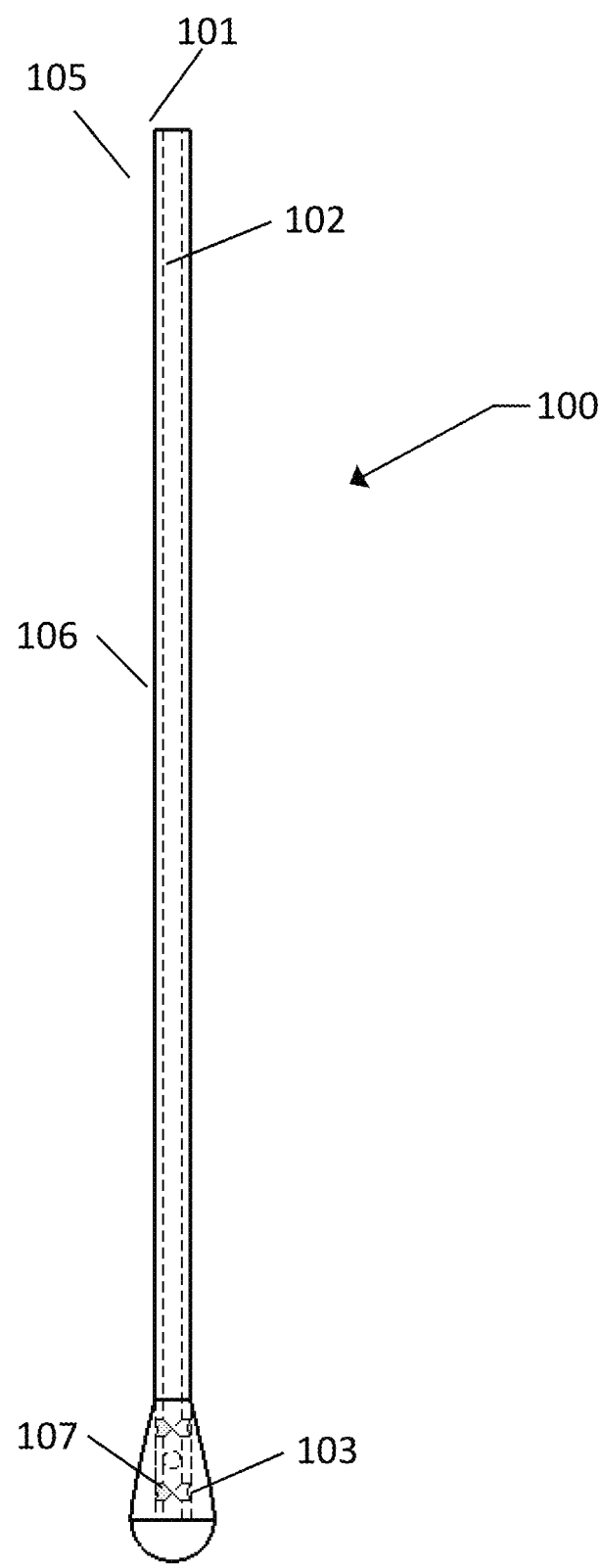
FIG. 2 shows a configuration of a hollow-shaft swab with holes through the side wall of the shaft tube to allow flow of foam through the entire swab head, according to an exemplary embodiment of the present subject disclosure.

FIG. 2 shows a custom designed hollow shaft swab 100 with a lumen 106 and holes 107 in the shaft wall 105 under the swab head 103. The holes 107 in the walls 105 of the shaft allow foam to more uniformly flow out through the entire swab head surface and therefor provide more complete elution of the entire swab head. The end of the shaft, under the swab head 103, may be open, completely sealed off or partially closed off to provide as uniform of flow throughout the entire swab head surface as possible. Additionally, the holes 107 may consist of one or more holes in the shaft wall 105 or may consist of a porous section of shaft produced by various manufacturing methods.

Figure 3:
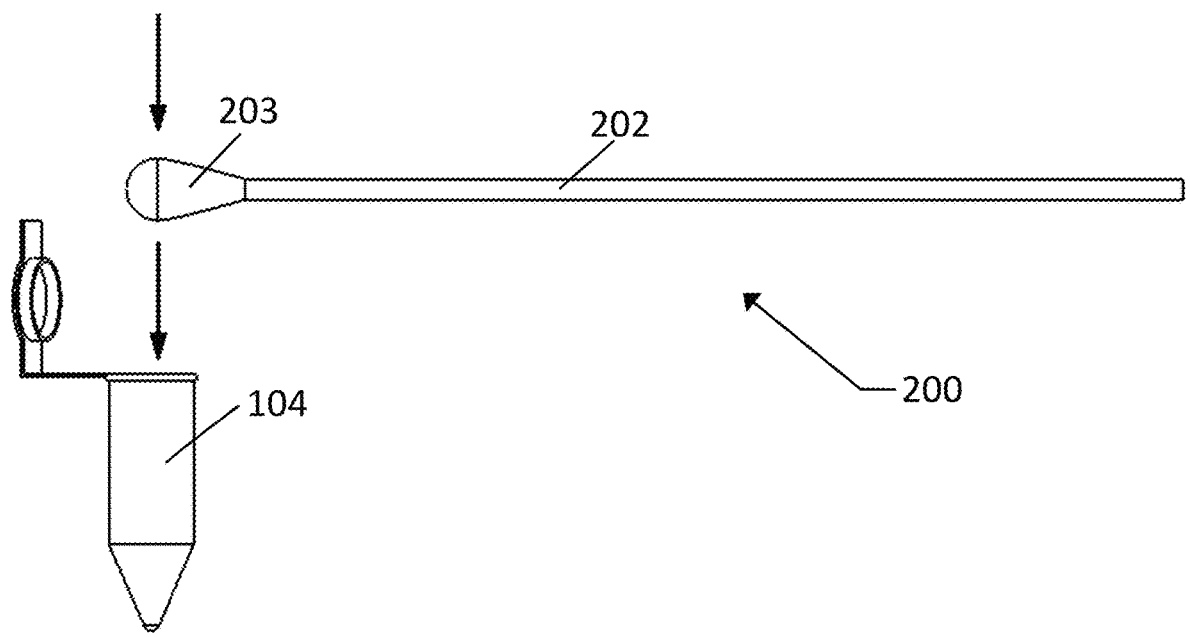
FIG. 3 shows the direction of wet foam elution flow across head of a swab, according to an exemplary embodiment of the present subject disclosure.

Elution of hollow swabs may be conducted in any direction with respect to foam flow. In one exemplary embodiment shown in FIG. 3, the direction of flow during elution across the outside surface of a swab head 203 of a swab 200 into a sample container 104 is generally perpendicular to the longitudinal axis of the shaft 202.

Figure 4:
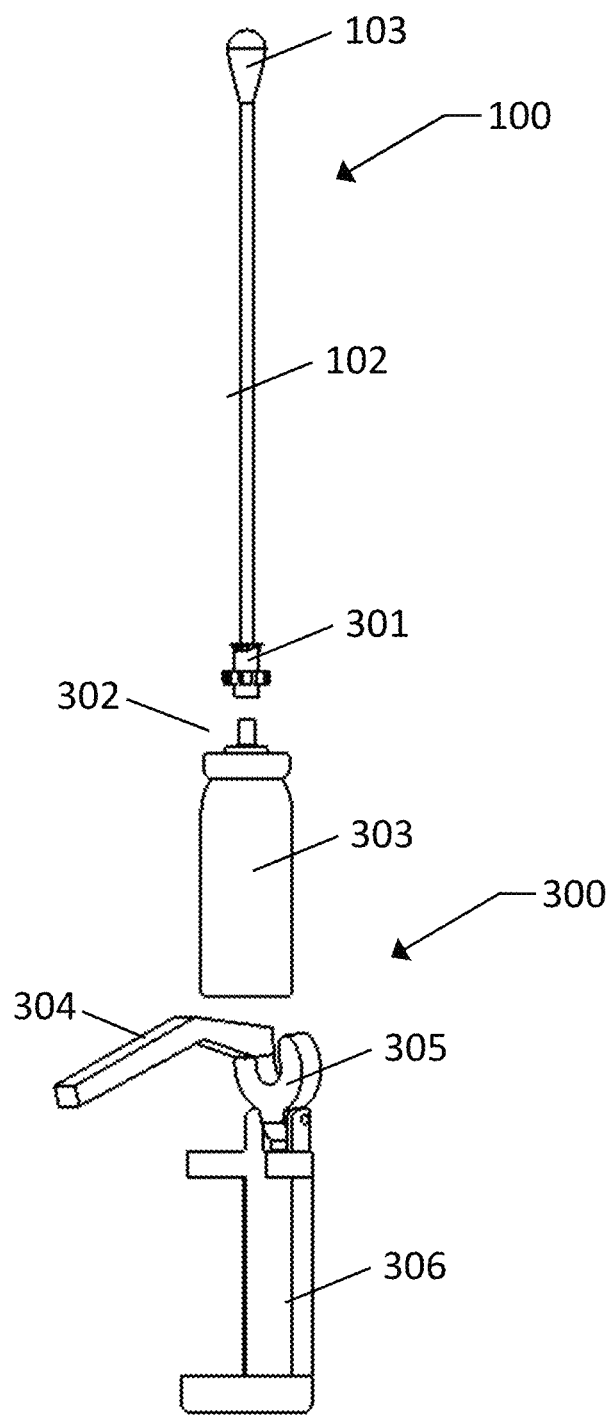
FIGS. 4 and 5 show a device for enabling surface collection and subsequent wet foam elution down the hollow shaft and out through the swab head for recovery of particles using hollow-shaft swabs, according to an exemplary embodiment of the present subject disclosure.
Figure 5:
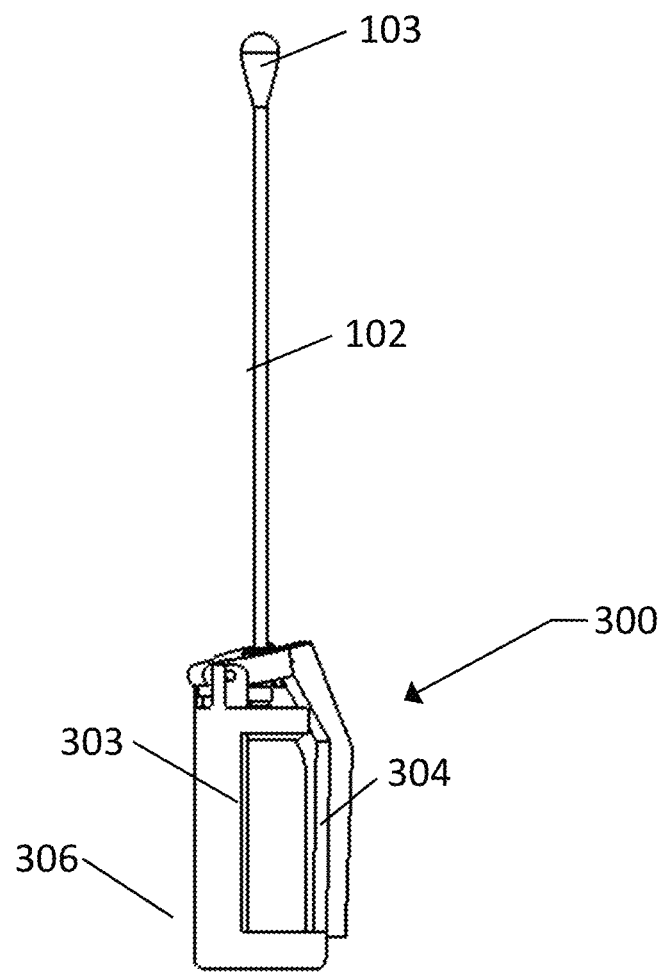
Figure 6:
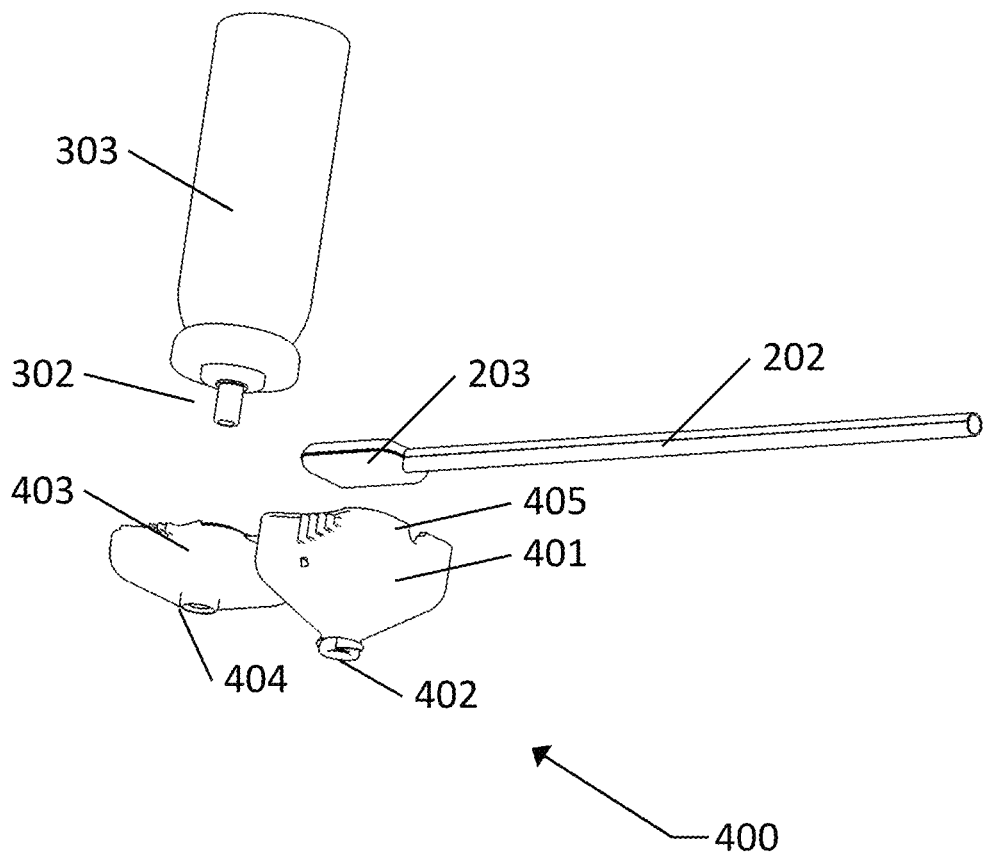
FIGS. 6-9 show a device for wet foam elution across the head of a swab for recovery of particles using swabs, according to an exemplary embodiment of the present subject disclosure.
Figure 7:
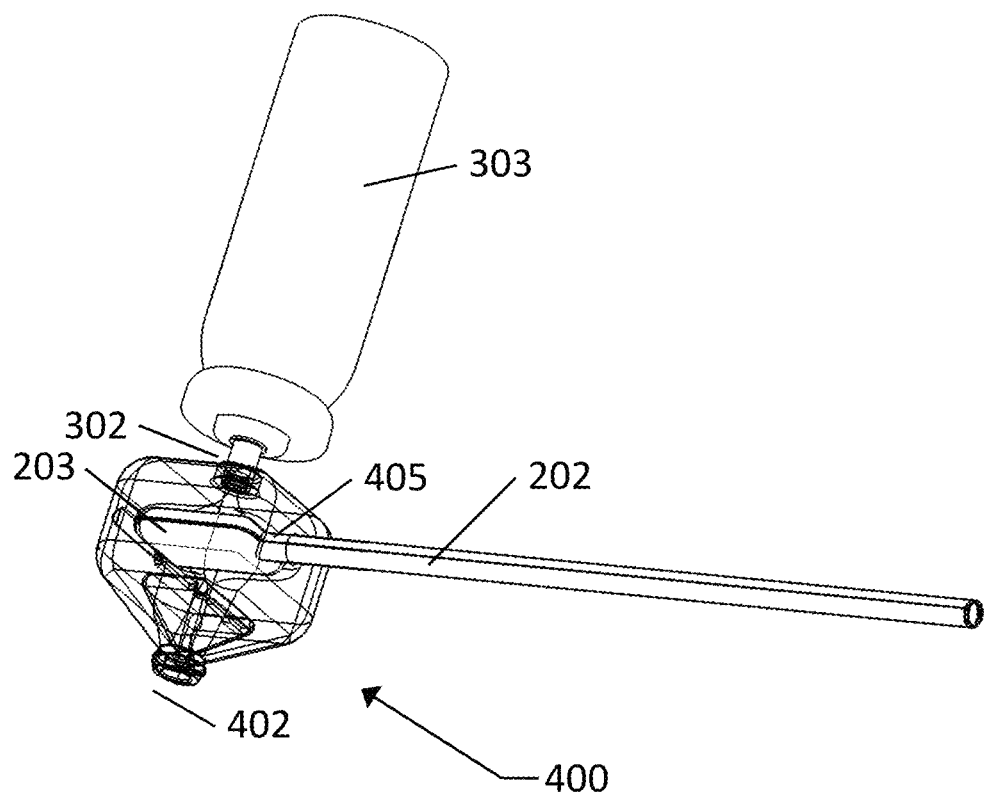
Figure 8:
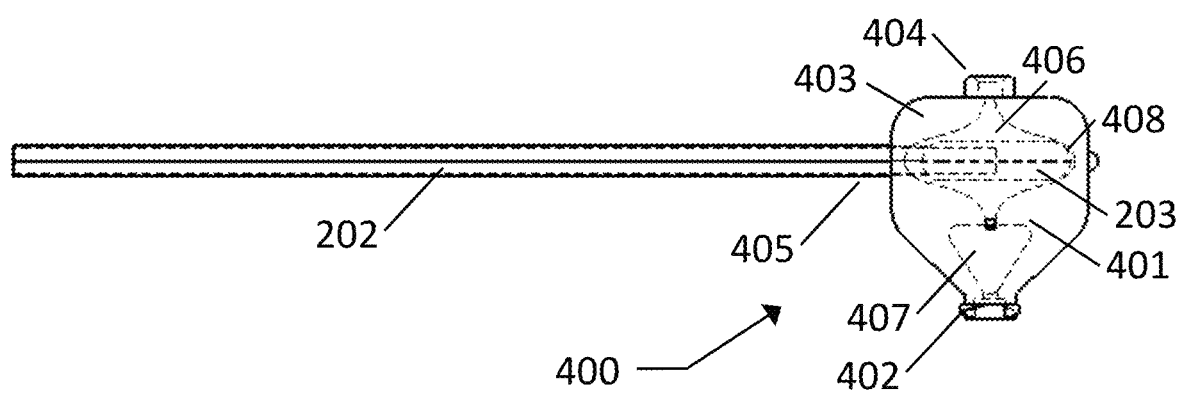
Figure 9:
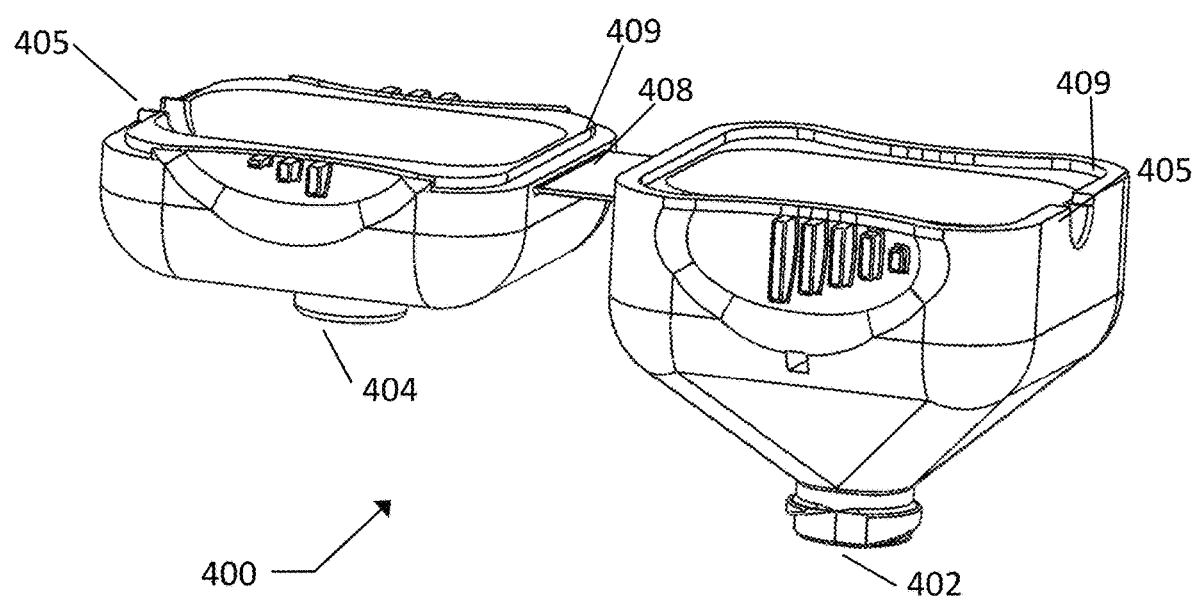

FIGS. 4 and 5 show a hollow shaft swab collection and elution tool 300 in conjunction with a hollow shaft swab 100. The collection and elution tool 300 holds a pressurized elution fluid canister 303, containing a wet foam elution solution under a pressurized soluble gas atmosphere, in the canister cradle 306 and in communication with the canister valve actuator 305. The pressurized elution fluid canister 303 may be a standard continuous release valve or a standard metered dose release valve. A hollow shaft swab 100 is attached to the valve stem 302 of the elution fluid canister 303 with the swab fitting 301. A user first uses the tool 300 to hold the swab 100 during sample collection. During the sample collection process the user may wet the swab head 103 by actuating the tool dispensing lever 304 to cause the canister valve actuator to push down on the elution fluid canister valve stem 302, thereby releasing elution fluid which travels down the lumen of the swab hollow shaft 102 and out through the swab head 102. This gives the user the capability of easily using the swab 100 in a dry or wet state.

In use, and following a sample collection, the tool 300 is then used to hold the swab head 103 in a sample container 104 and the user then actuates the dispensing lever 304 to release elution fluid in the form of a wet foam, which travels down the lumen of the swab hollow shaft 101 and out through the swab head 102. In the process particles that were earlier collected onto the swab head surface 103 are now recovered into a small volume of foam, which breaks down into a small liquid sample.

In alternative embodiments of the hollow shaft swab collection and elution tool 300, an integral swab ejector button or lever may be added to allow the user, following swab elution, to easily eject the used swab into a waste container. In another exemplary embodiment, the tool 300 may include a mechanism for allowing the user to push the tool onto a new swab while holding only the tool, much like commercially available micro-pipettors, such as those produced and sold by Eppendorf, which are held while pushing them onto a pipette tip contained in a pipette tip box. One example of a micro-pipettor of this type is the Eppendorf family of pipettors. In this embodiment the operation will be familiar to those familiar with micro-pipettors that allow a user to push a pipette tip onto the instrument, then use the pipettor and pipette to acquire a set sample volume, prior to ejecting the used pipette into a waste container. In such an embodiment of the hollow shaft swab collection and elution tool, a user would push the tool onto the swab, actuate the foam lever or button to wet the swab head, collect a surface sample, hold the swab head in a sample container, actuate the foam lever or button to elute the sample into the container, hold the swab over a waste container and actuate the swab ejector button or lever to release the used swab into the waste container.

In another alternative embodiment of the hollow shaft swab collection and elution tool 300, the system may contain mechanical or electro-mechanical mechanism of releasing a small set volume of elution fluid from the pressurized elution fluid canister 303. This can be performed with mechanical based systems such as an integral sample reservoir or sample loop that holds a set volume of elution fluid after release from the aerosol canister and then releases this set volume during the elution process. Alternatively the system may use a standard electromechanical valve, such as those manufactured by Bio-Chem Fluidics Inc., to release a set volume during the elution process. In this case the foam is released by opening the valve for a defined period of time so that a reproducible volume of the elution fluid is released through an integral control orifice.

The hollow shaft swabs used in these systems may be especially configured to improve the elution process. This may include use of different swab materials, such as flocked materials, that improve elution and have the correct pressure drop to allow the wet foam through, but allow the foam to flow more evenly through the entire swab head surface area. Additionally, the hollow shaft 102 may be configured with a porous area or specifically sized holes under the swab head 103 material that allow the foam to be evenly released throughout the collect zone of the swab head. A hole at the end of the swab shaft may be included to allow foam to contact the end of the swab. This hole may be the same size or smaller than the shaft lumen.

Testing of a prototype hollow shaft swab collection and elution tool 300 prototype was performed with 3.0 µm nominal diameter yellow-green fluorescent polystyrene microspheres spiked onto a melamine resin-coated Masonite coupon and allowed to dry. The microspheres were swabbed from the surface, using a standard swabbing approach while holding the swab in the collection and elution tool 300, and then recovered into a small volume of elution fluid using the prototype tool. A UV light was then placed over the tubes to make the captured microspheres more visible. From this simple test it was clear that the swab sample contained significant quantities of microspheres collected from the surface.

FIGS. 6-9 show an exemplary embodiment of a cartridge type swab elution device 400 which uses a flow of foam across the face of the swab head 203 to elute. The user first swabs a target surface and then places the swab into the clam-shell cartridge 401. The cartridge 401 contains a living hinge 408 on one side and sealing surfaces 409 around the elution chamber 406. The user closes the clam-shell cartridge 401 until it is latched and sealed. Aperture 405 is designed to accommodate the shaft 202 while the clam-shell cartridge 401 is closed. The user then attaches the luer adapter 402 to a separate sample container or assay cartridge, or holds the cartridge over a sample tube. The valve stem 302 of a pressurized elution fluid canister 303, with a metering valve, as is commonly available, is then pushed into the top port 404 located on a top lid portion 403 of the cartridge, releasing a set volume of elution fluid. The elution fluid quickly expands into a larger volume of wet foam, and under the pressure created by the propellant gas coming out of solution, is forced to flow over and around the swab head 203. The foam then flows into a foam collapsing reservoir 407 below the swab head 203 and out into a sample container or secondary cartridge.

Many alternate embodiments of the cartridge type swab elution device can be envisioned by one skilled in the art. In one embodiment the elution fluid can be held in the foam collapsing reservoir 407 until needed, at which time it is drawn out and into a secondary assay cartridge or sample reservoir. In another embodiment, a similar cartridge can be built that would be eluted by insertion of the cartridge into an elution instrument that contains a larger elution fluid canister and a timed valve to allow for precise control of the elution fluid volume released. In another embodiment, the cartridge could be part of a larger assay cartridge containing the elution system, other sample preparation operations and the assay components. In this way after sampling the user could place the swab into a cartridge which would be inserted into an instrument. The instrument would then run through the elution process, sample preparation steps and assay steps. The target materials would remain within the cartridge throughout the process.

In another embodiment, the cartridge may be used for elution of hollow shaft swabs. The user would then use a hollow swab shaft, an integrated cutting blade to cut the swab shaft, and a mechanism for fluidically connecting the pressurized foam canister to the lumen of the hollow swab shaft that would allow elution foam to be introduced into the shaft lumen and then out through the swab head.

Many other embodiments of the swab elution devices and methods can be envisioned including the use of dual swabs (two swabs connected together) for collection of duplicate samples or samples from both nares of a single patient at the same time for instance. Additionally many different sizes, shapes and configurations of swabs, including different material types, may be used—including very large and very small swabs. Different shaped swabs may also be used including scoop shaped or spiral shaped for improved collection in certain applications.

Figure 10:
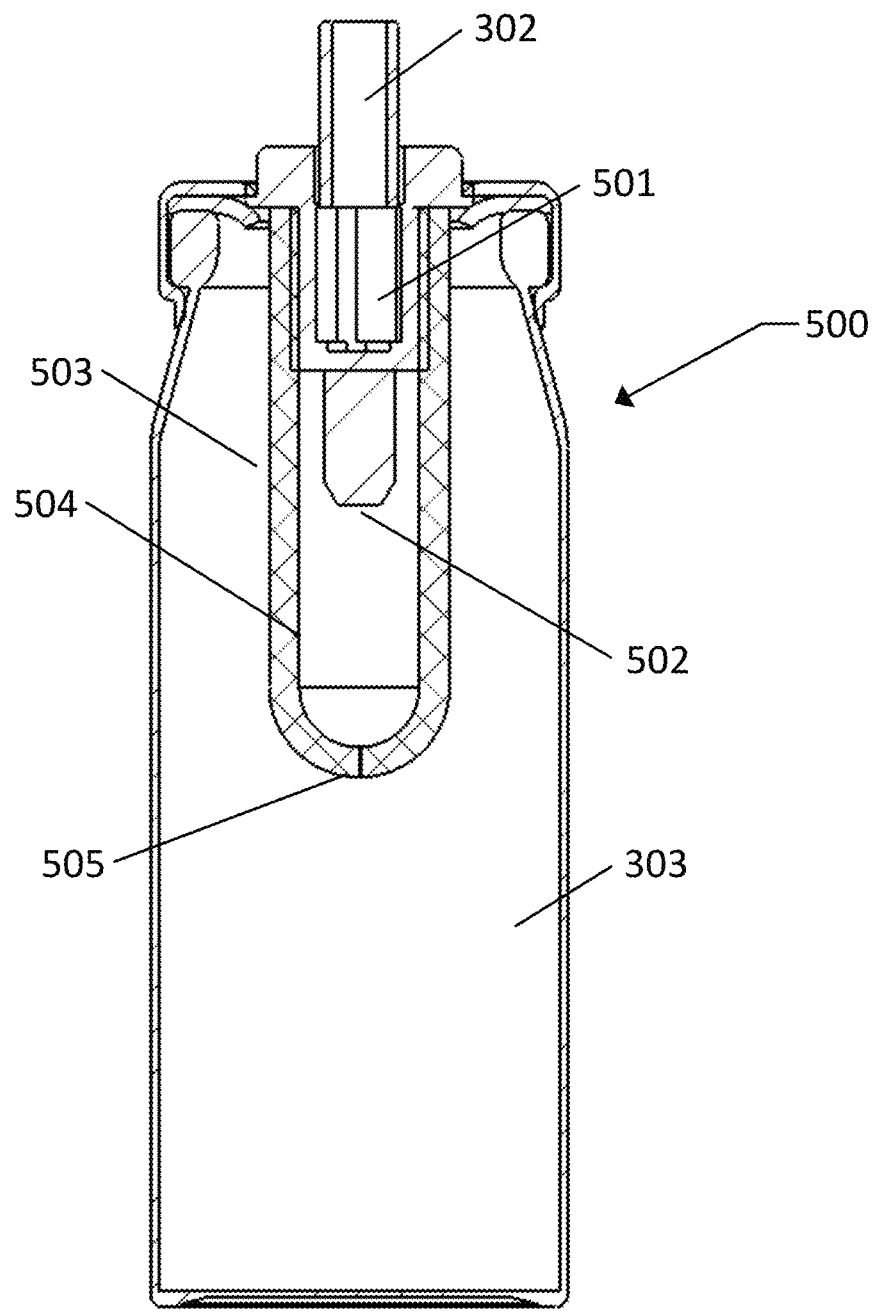
FIG. 10 shows a hand-held wet foam elution canister with an internal pouch for delivering a set volume of elution fluid, according to an exemplary embodiment of the present subject disclosure.

FIG. 10 shows an exemplary embodiment of a novel pouch-on-valve aerosol canister 500 which provides a mechanism of delivering a small set volume from the portable pressurized elution fluid canister 30, described throughout this disclosure. The aerosol canister 500 includes a standard continuous release aerosol valve 501 and a standard valve stem 302. Enclosed within the canister 303 and attached to the base of the valve 501 and enclosing the valve inlet 502 to create fluid reservoir 504 is a silicone rubber or other flexible material pouch or bag 503. To fill pouch-on-valve aerosol canisters 500 during manufacture, pressurized gas is pushed into the valve stem 302, through the valve 501, into the reservoir 504 and through the orifice 505 and finally into the canister 303, until a set pressure is reached. Upon reaching the set pressure, fluid saturated with the propellant gas is pushed through the valve 302 and into the reservoir 504 until a set volume of fluid has been pushed in. The volume of fluid pushed in is such that reservoir 504 is overfilled, such that any additional fluid passes through orifice 505 into canister 303. During use, valve stem 302 is depressed and held in a depressed position until flow of liquid and gas stops. When valve stem 302 is depressed fluid flows quickly from reservoir 504 out through valve 501 and is dispensed from valve stem 302. When the volume of fluid contained in reservoir 504 has been dispensed the flexible reservoir 504 becomes compressed due to the higher pressure of gas in the canister 303. Compression of the reservoir 504 causes it to act like a check valve and stop flow of gas from the aerosol canister 500.

Figure 11:
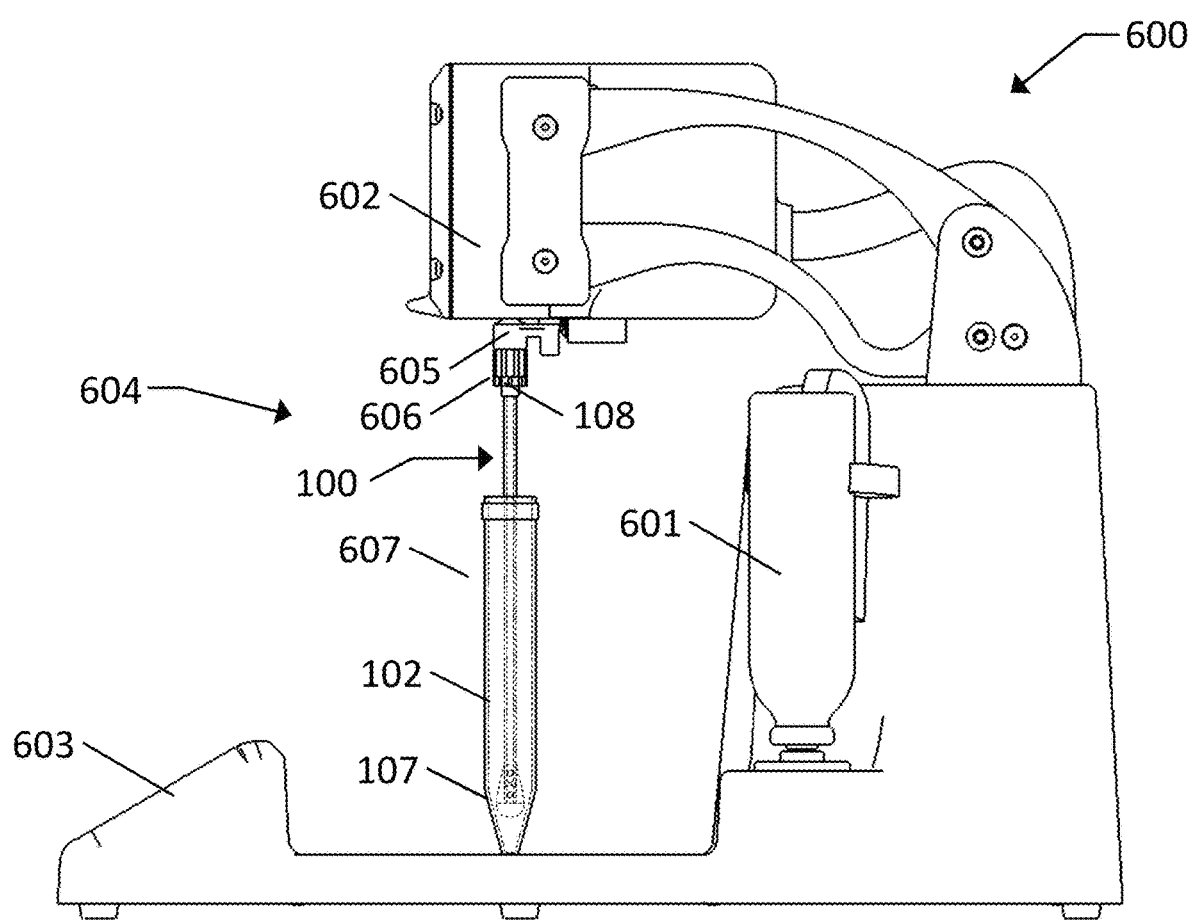
FIGS. 11 and 12 show a consumable for hollow shaft swab elution using wet foam dispensed from Applicant's Concentrating Pipette Instrument, according to an exemplary embodiment of the present subject disclosure.
Figure 12:
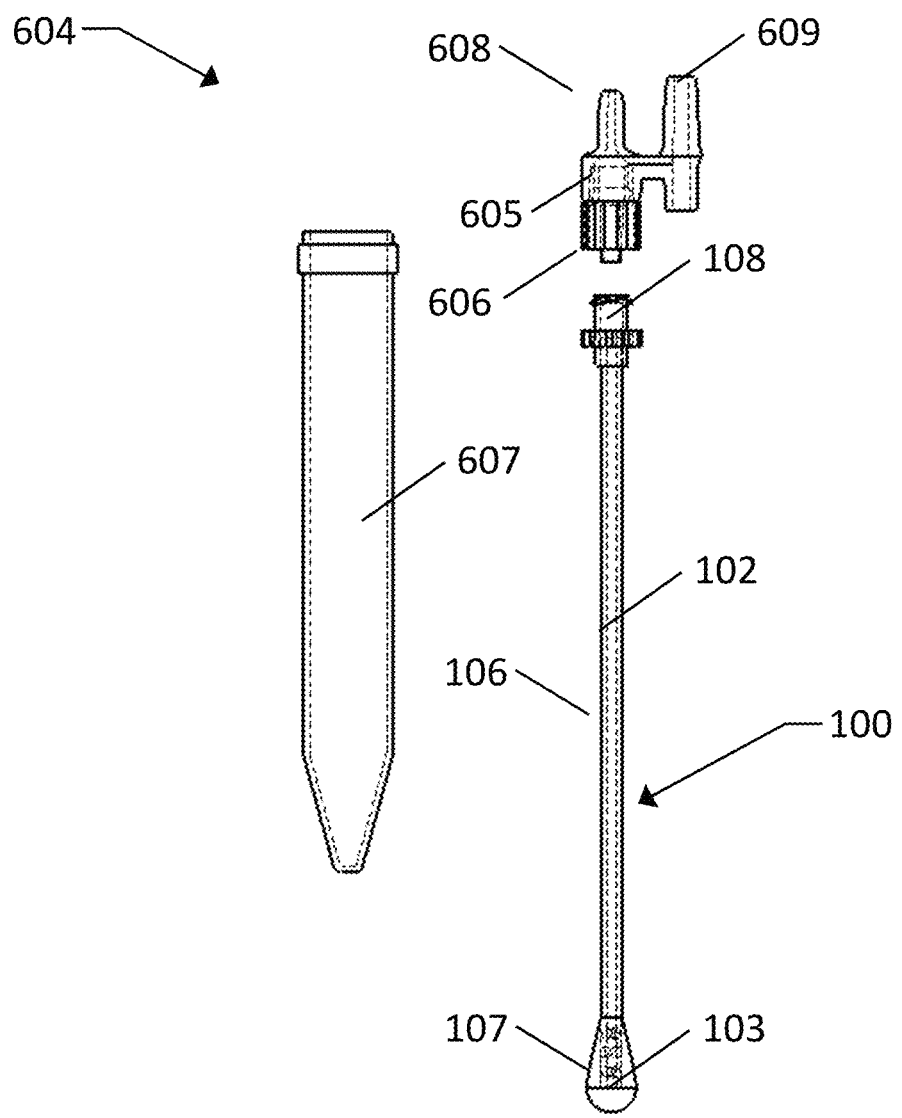

FIGS. 11 and 12 show an exemplary embodiment of a hollow shaft swab elution device 604 for use with Applicant's Concentrating Pipette System 600. Hollow shaft swab 100 is attached to the elution device 604 by connecting fitting 108 to fitting 606. The swab 100 may be used prior to connecting it to the elution device 604 or the two may be connected and packaged for use together. After collection of a surface sample, the two nipples 608 and 609 on the fitting 605 are inserted into the Concentrating Pipette 600 head 602. After insertion, the user interface 603 is used to set the elution fluid setpoints to allow the appropriate volume of elution fluid to be dispensed and an elution is performed. Elution fluid is released by an electromechanical elution fluid valve within the Concentrating Pipette 600 from the pressurized elution fluid canister 601. Elution fluid is released in the form of wet foam and travels through elution fluid nipple 608, fittings 606 and 108 and through the lumen 106 of the hollow shaft 102 and out through shaft holes 107 and the swab head 103. As the foam flows out through the swab head 103 captured particles are recovered into the foam and dispensed into the reservoir 607.

Figure 13:
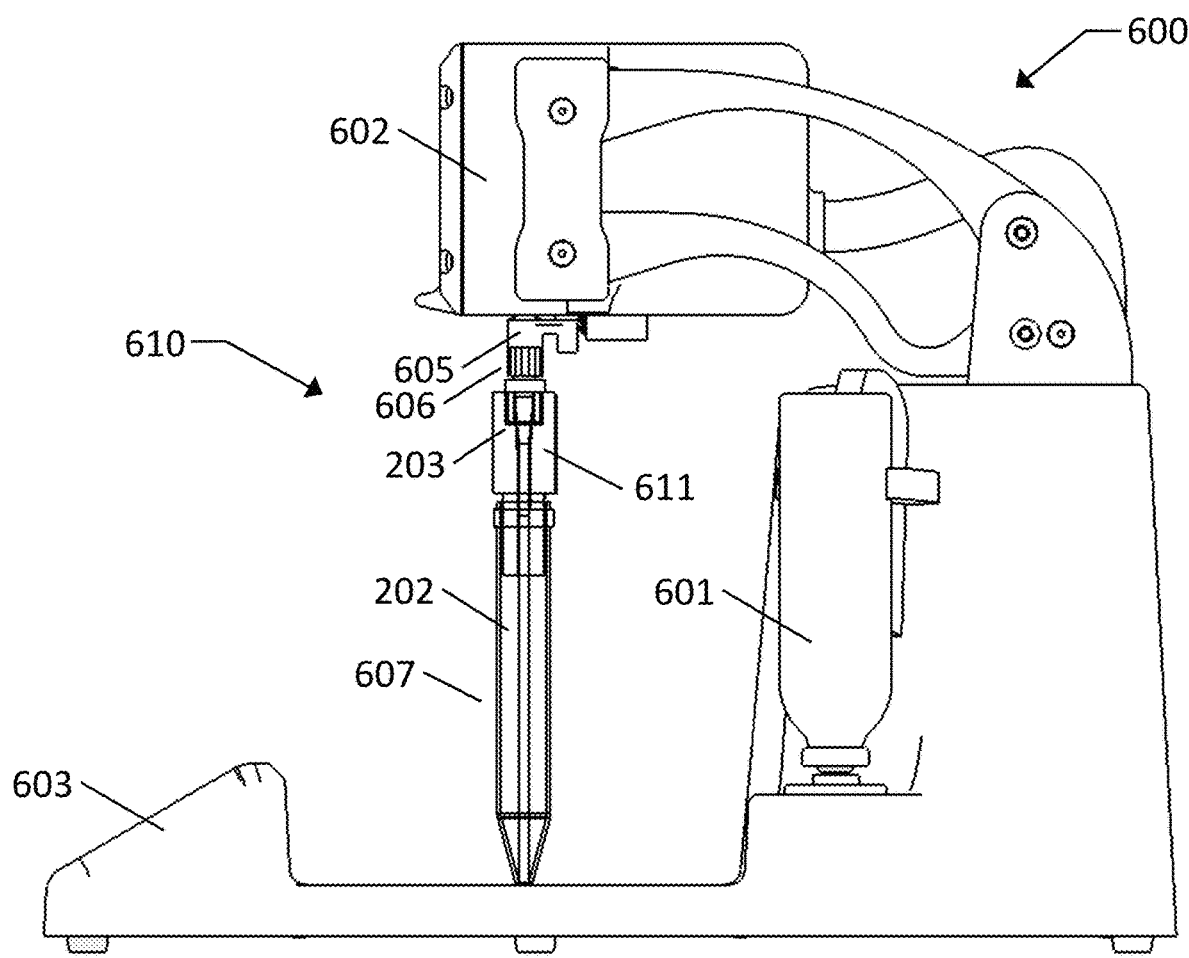
FIGS. 13 and 14 show a consumable for swab elution performed by a flow of foam across the swab head using wet foam dispensed from Applicant's Concentrating Pipette Instrument, according to an exemplary embodiment of the present subject disclosure.
Figure 14:
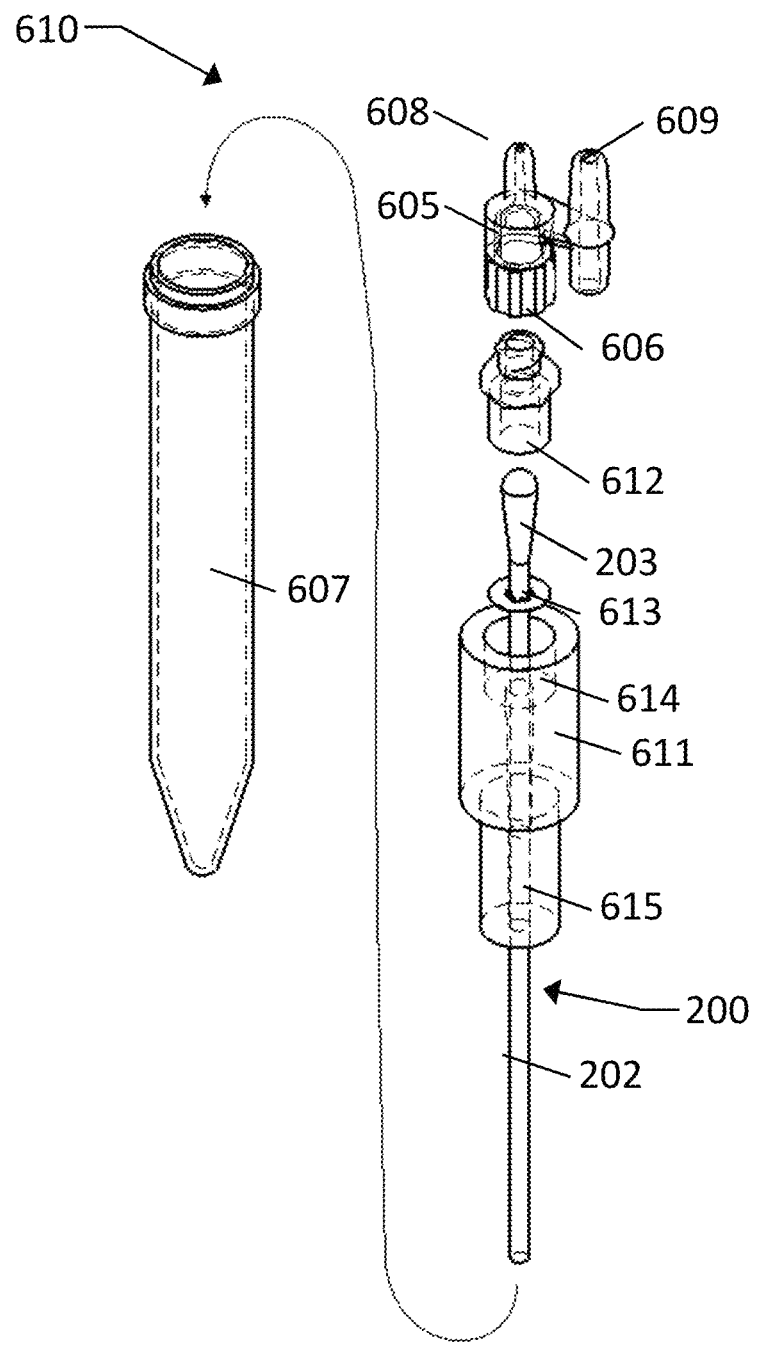

FIGS. 13 and 14 show an exemplary embodiment of an across the head swab elution device 610 for use with the Applicant's Concentrating Pipette System 600. After collection of a sample with swab 200, the shaft 202 of the swab 200 is placed through star-ring 613 and into fitting 615 and dropped into place such that swab head 203 is within chamber 614 in fitting 611. Fitting 612 is then screwed into fitting 611. This assembly allows the swab head 203 to rest against star-ring 613 and in the center of chamber 614. Star-ring 613 keeps the swab head 203 from being pushed into the flow path below chamber 614 during the elution process and allows wet foam to flow around all sides of the swab head 203. Fitting 612 is then attached to fitting 606 and the two nipples 608 and 609 on the fitting 605 are inserted into the head 602 on Concentrating Pipette System 600. After insertion, the user interface 603 is used to set the elution fluid setpoints to allow the appropriate volume of elution fluid to be dispensed and an elution is performed. Elution fluid is released by an electromechanical elution fluid valve within the Concentrating Pipette System 600 from the pressurized elution fluid canister 601. Elution fluid is released in the form of wet foam and travels through the internal flow path of nipple 608, fitting 605, fitting 612, past swab head 203, past star-ring 613 and out through the flow path of fittings 611 and 615. The captured particles are recovered into the foam and dispensed into the reservoir 607.

Figure 15:
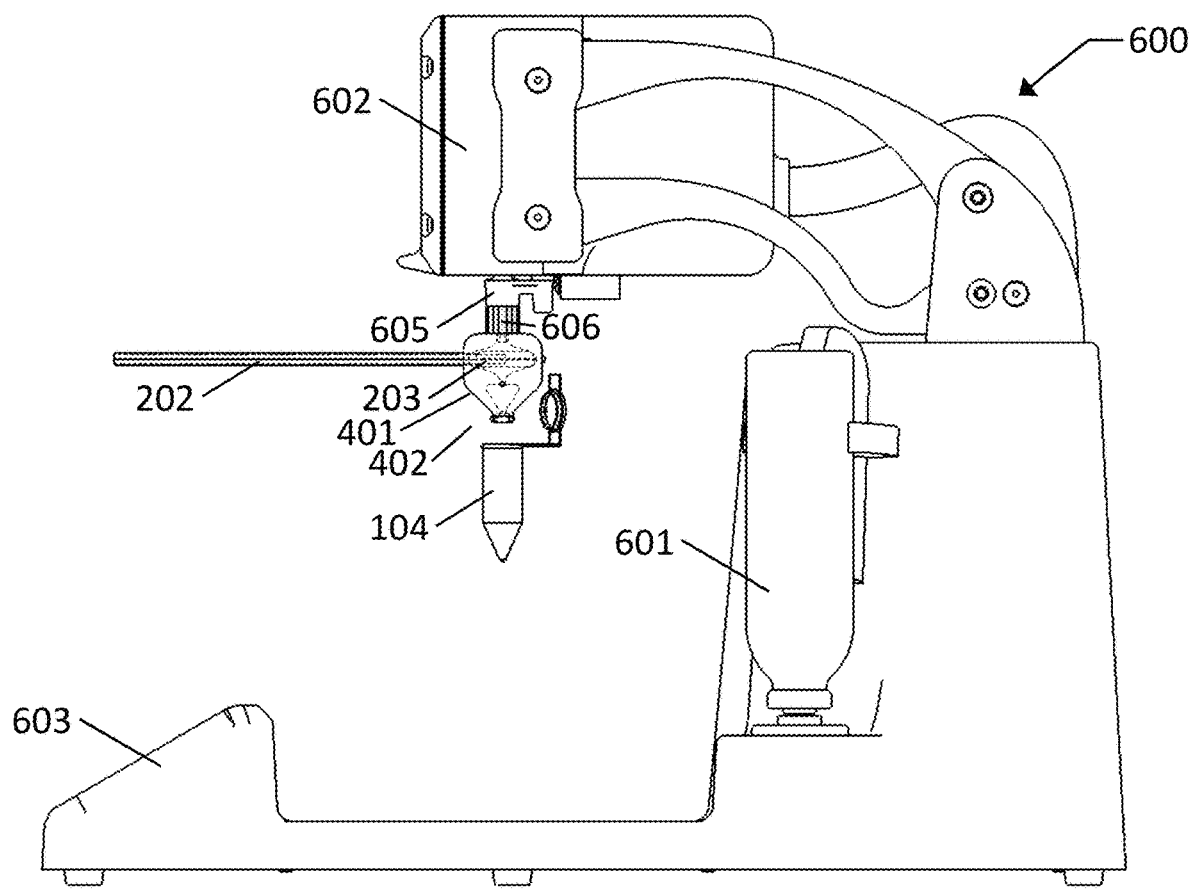
FIGS. 15 and 16 show another configuration of a consumable for swab elution performed by a flow of foam across the swab head using wet foam dispensed from Applicant's Concentrating Pipette Instrument, according to an exemplary embodiment of the present subject disclosure.
Figure 16:
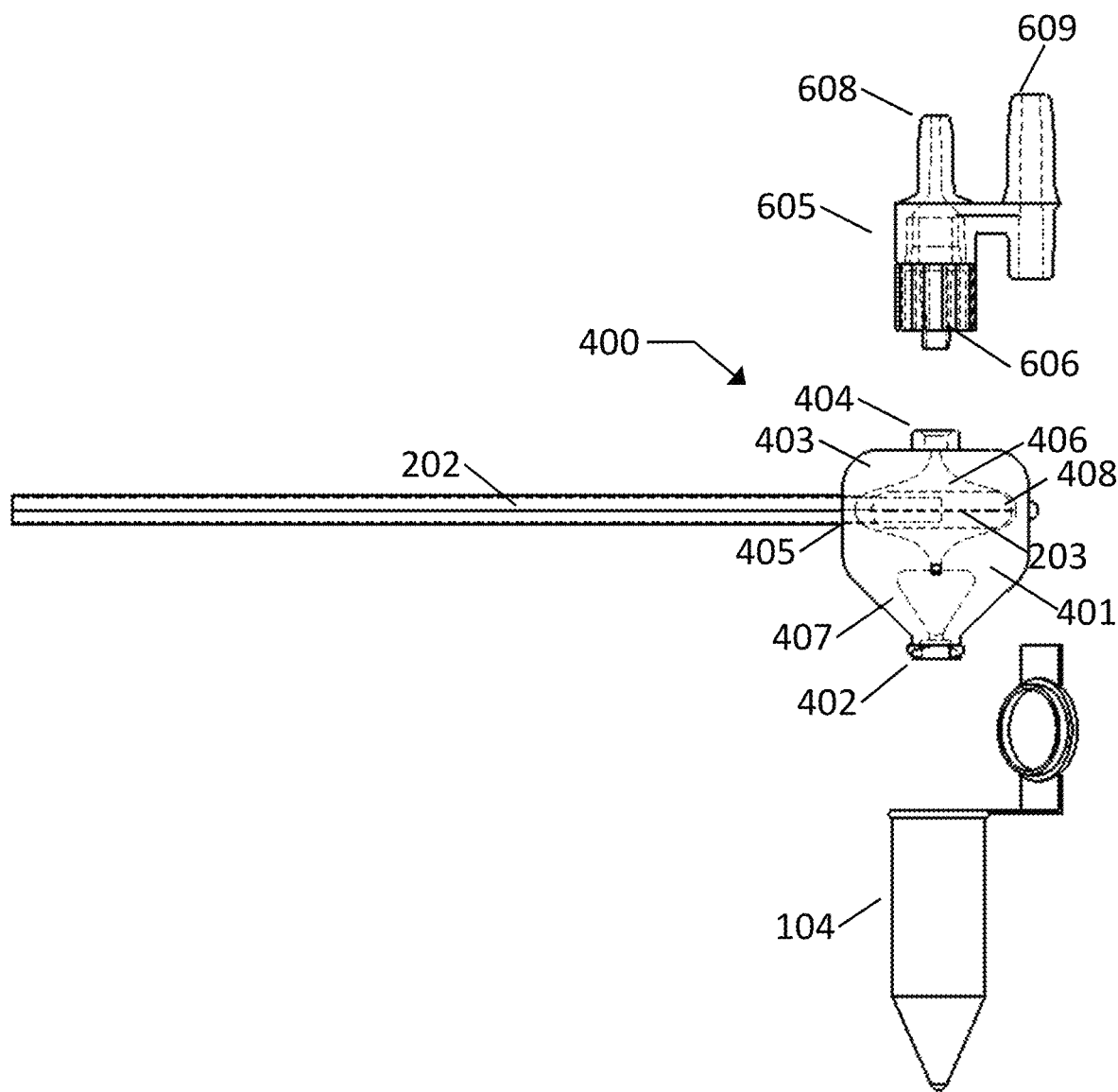
Figure 17:
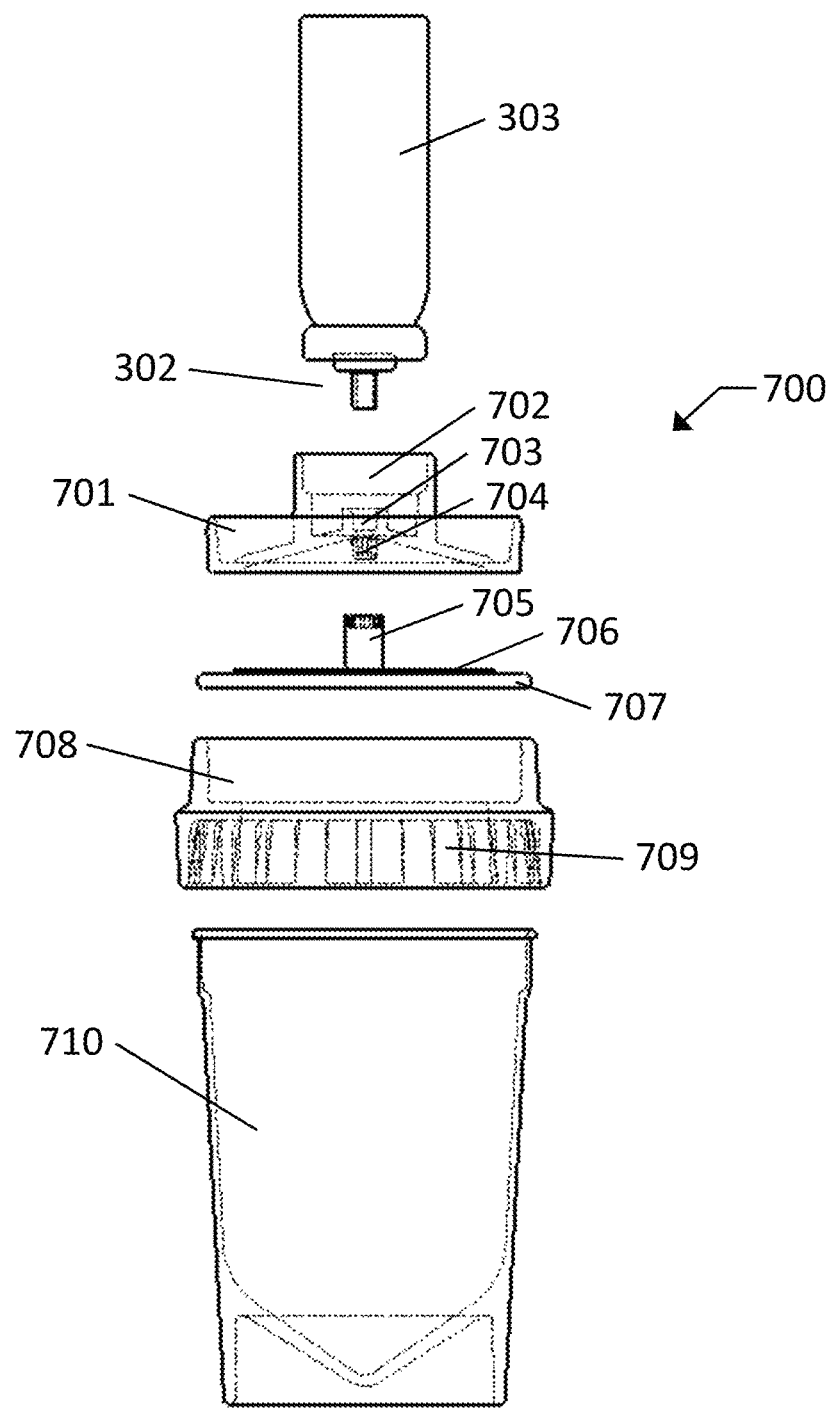
FIGS. 17-25 show a consumable surface wipe and elution device and various components with a thin wipe material and a vented sample cup for catching the elution fluid, according to an exemplary embodiment of the present subject disclosure.
Figure 18:
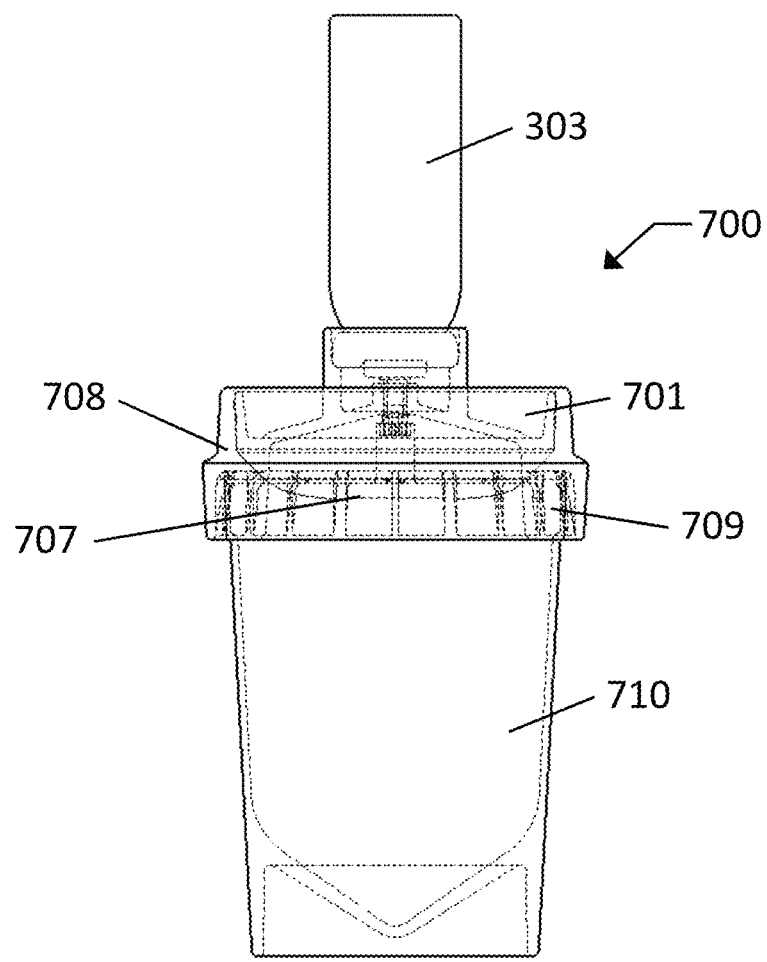
Figure 19:
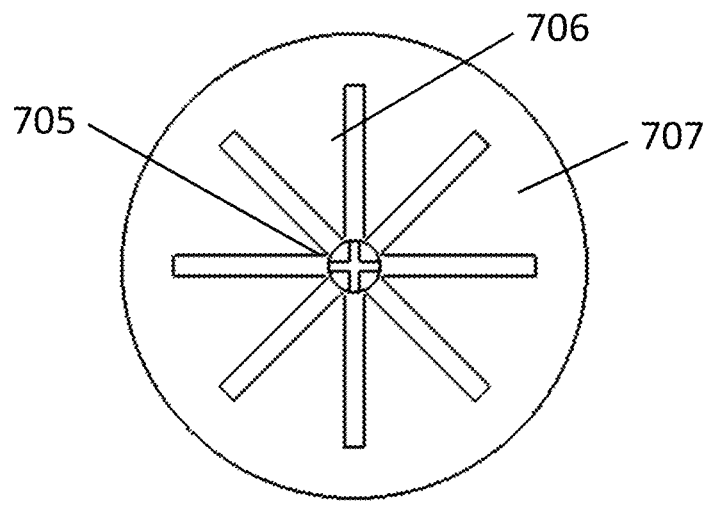
Figure 20:
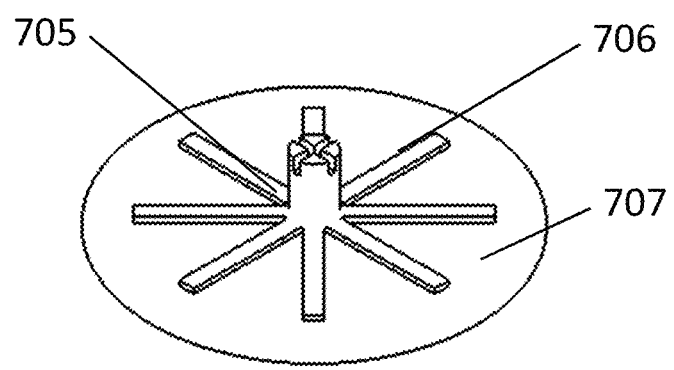
Figure 21:
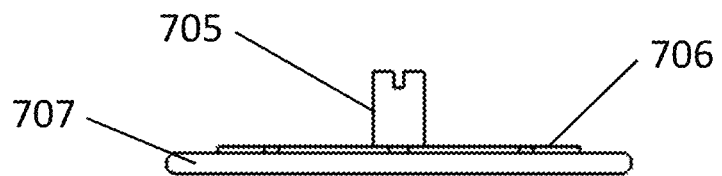
Figure 22:
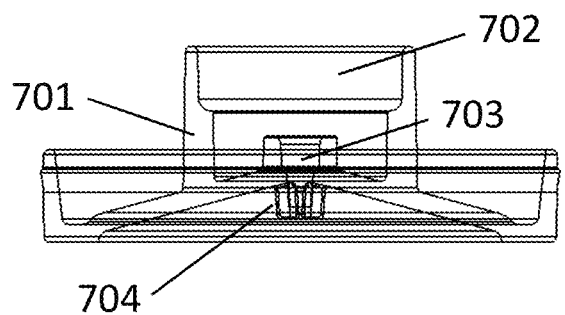
Figure 23:
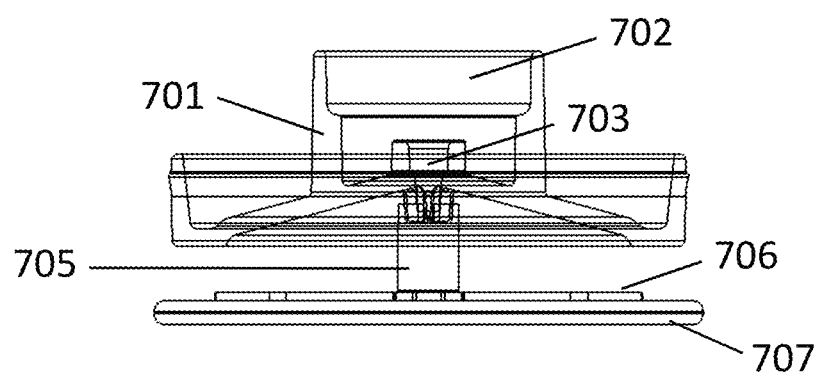

FIGS. 15 and 16 show an exemplary embodiment of use of the across the head swab elution device 400 (shown in FIGS. 6-9) with Applicant's Concentrating Pipette System 600 performing elution rather than a stand-alone pressurized elution fluid canister. The user first swabs the surface and then places the swab into the clam-shell cartridge 401. The cartridge contains a living hinge 408 on one side and sealing surfaces 409 around the elution chamber 406. The users close the clam-shell cartridge until it is latched and sealed. Fitting 404 is then attached to fitting 606 and the two nipples 608 and 609 on the fitting 605 are inserted into the head 602 of the Concentrating Pipette System 600. After insertion, the user interface 603 is used to set the elution fluid setpoints to allow the appropriate volume of elution fluid to be dispensed and an elution is performed. Elution fluid is released by an electromechanical elution fluid valve within the Concentrating Pipette System 600 from the pressurized elution fluid canister 601. Elution fluid is released in the form of wet foam and travels through the internal flow path of nipple 608, fitting 606, fitting 404, and is forced to flow over and around the swab head 203 within chamber 406. The foam then flows into a foam collapsing reservoir 407 and the captured particles are recovered into the foam and it is dispensed into a sample container 104.

Wipe Collection/Elution

Figure 24:
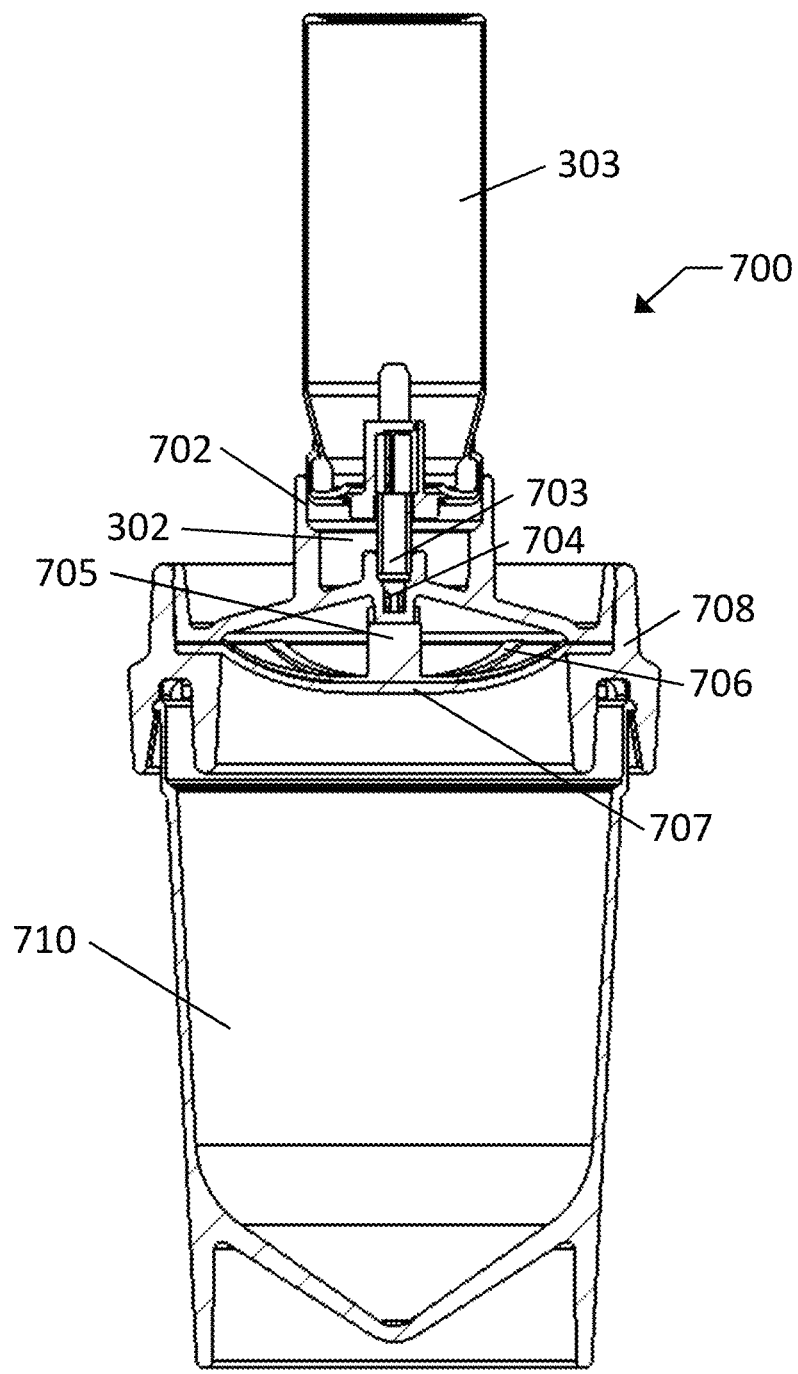
Figure 25:
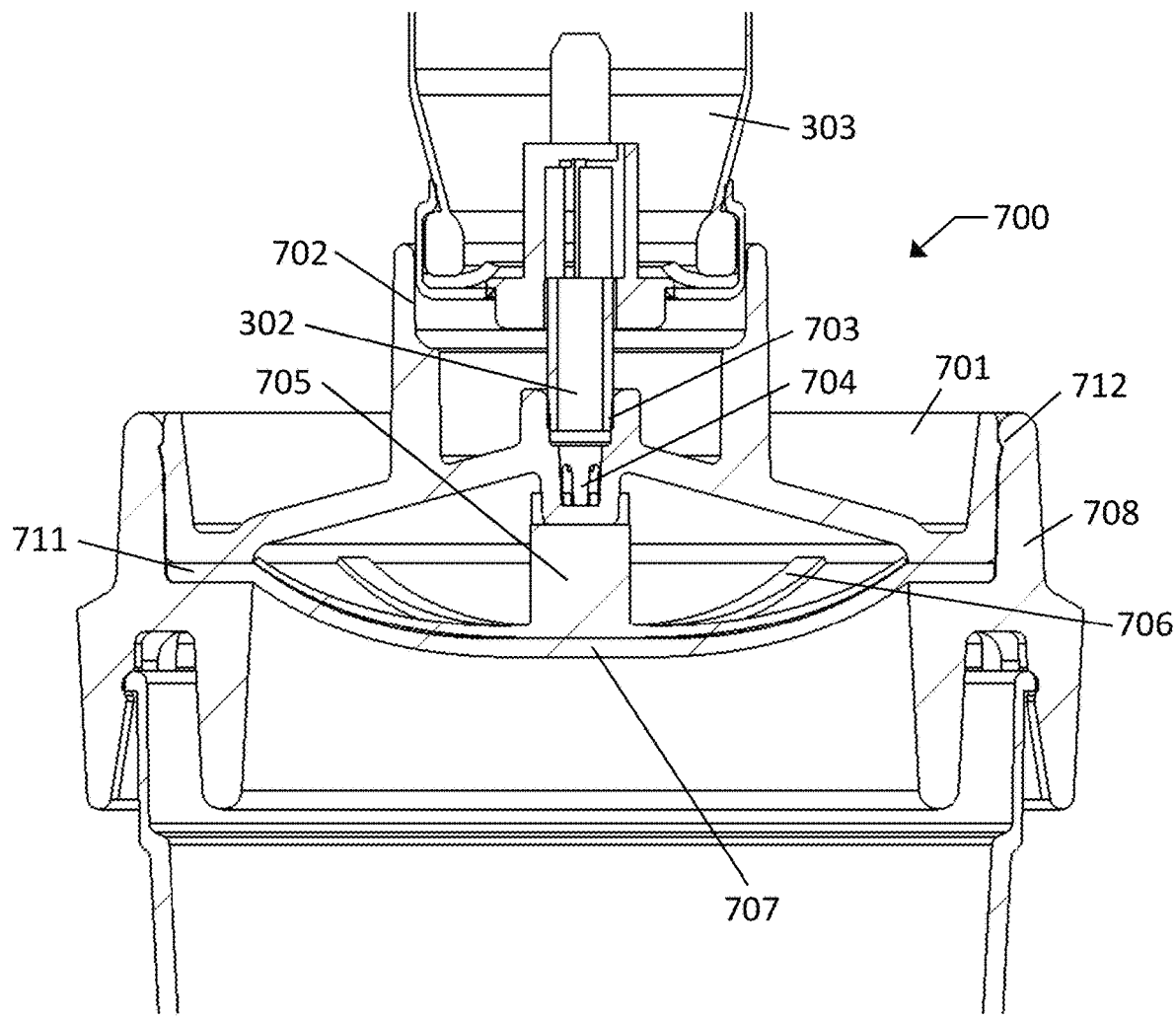

FIGS. 17 through 25 show an exemplary embodiment of a surface wipe collection and recovery device 700. Surface wipe material 707 is a non-woven, woven or open cell foam material with support 706 and attachment post 705. For collection of surface samples, a user holds onto attachment post 705 and support 706, or attaches attachment post 705 to elutor cap 701 and uses elutor cap 701 as a handle. A surface sample is then collected with the dry surface wipe material 707 or pre-wets the material or the surface with water, surfactant solution or other appropriate buffer solution. The surface sample is collected from an appropriate area and the attachment post 705 is attached to elutor cap 701 (if not already attached). Elutor cap 701 and wipe material 707 are then inserted into elutor ring 708 and snapped into place with snap fit 712. When snapped into place, wipe material 707 becomes compressed as shown as 711 between elutor cap 701 and elutor ring 708, as seen in FIG. 25. The combination of the attachment post 705, support material 706 and wipe material 707 are flexible so that once locked into position, the original flat geometry flares into a convex geometry, as shown in FIGS. 24 and 25. Compression of the wipe material 707 acts to keep elution foam from passing around the edge of the wipe material during the sample recovery process. The elutor ring 708 is then attached to sample cup 710. The hand-held pressurized elution fluid canister 303 is then placed into fitting 702 and the user pushes down on the canister 303 to actuate valve stem 302 against valve stem port 703. Upon actuation, the valve stem 302 releases elution fluid which passes through flow splitter 704. Flow splitter 704 acts to push the elution fluid, which is rapidly turned into wet foam away from the center flow path, so that it distributes evenly as it flows down and through the wipe material 707, recovering particles that were captured from the surface into the material. The foam is then dispensed into sample cup 710 and quickly breaks back down into a liquid sample. Gas vents 709 allow gas released from the wet foam to escape from the assembly, so that the entire assembly remains at or near to atmospheric pressure.

Figure 26:
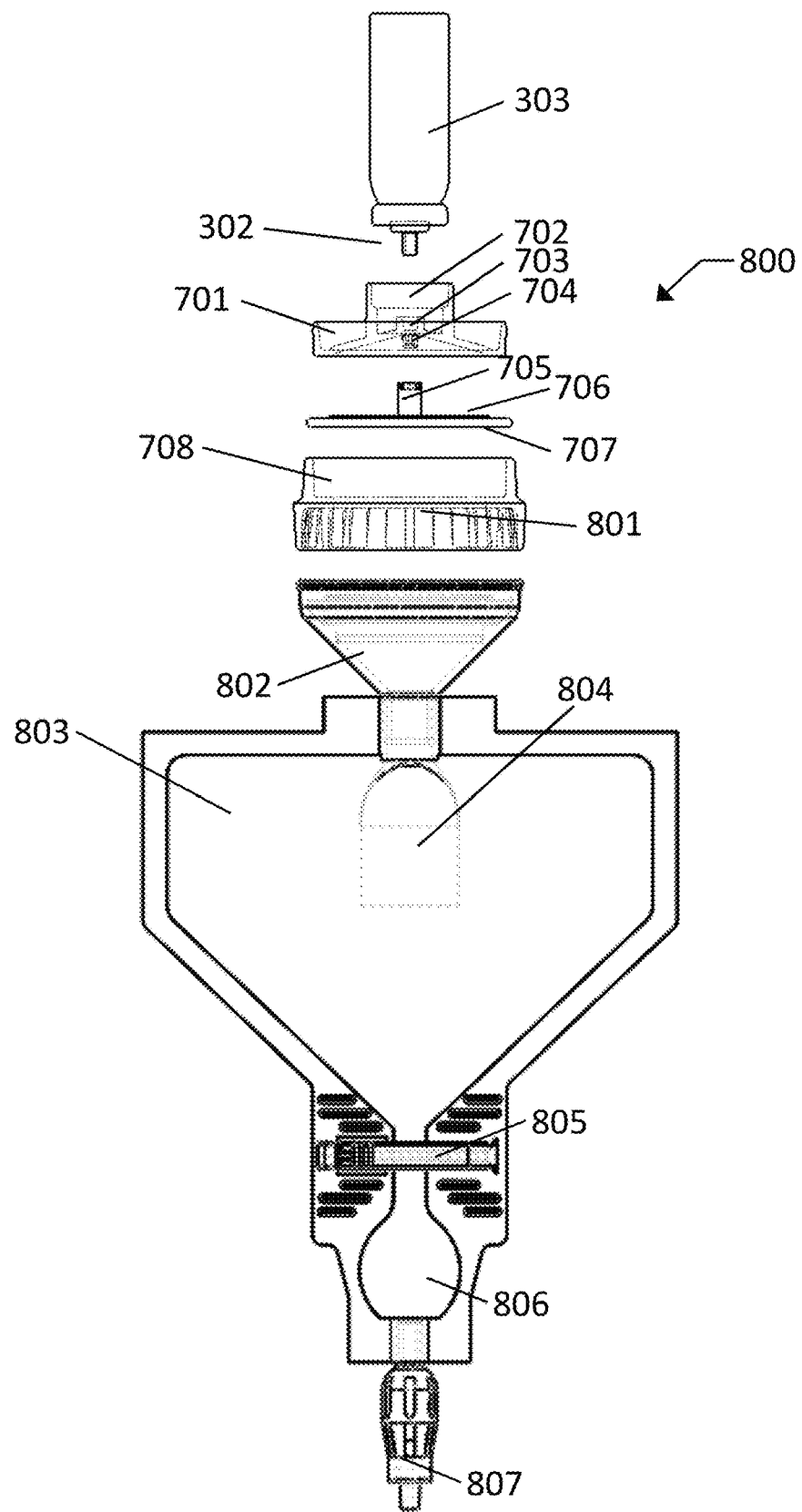
FIGS. 26-28 show a consumable surface wipe and elution device with a flexible bag for catching the elution fluid and delivering a sample aliquot, according to an exemplary embodiment of the present subject disclosure.
Figure 27:
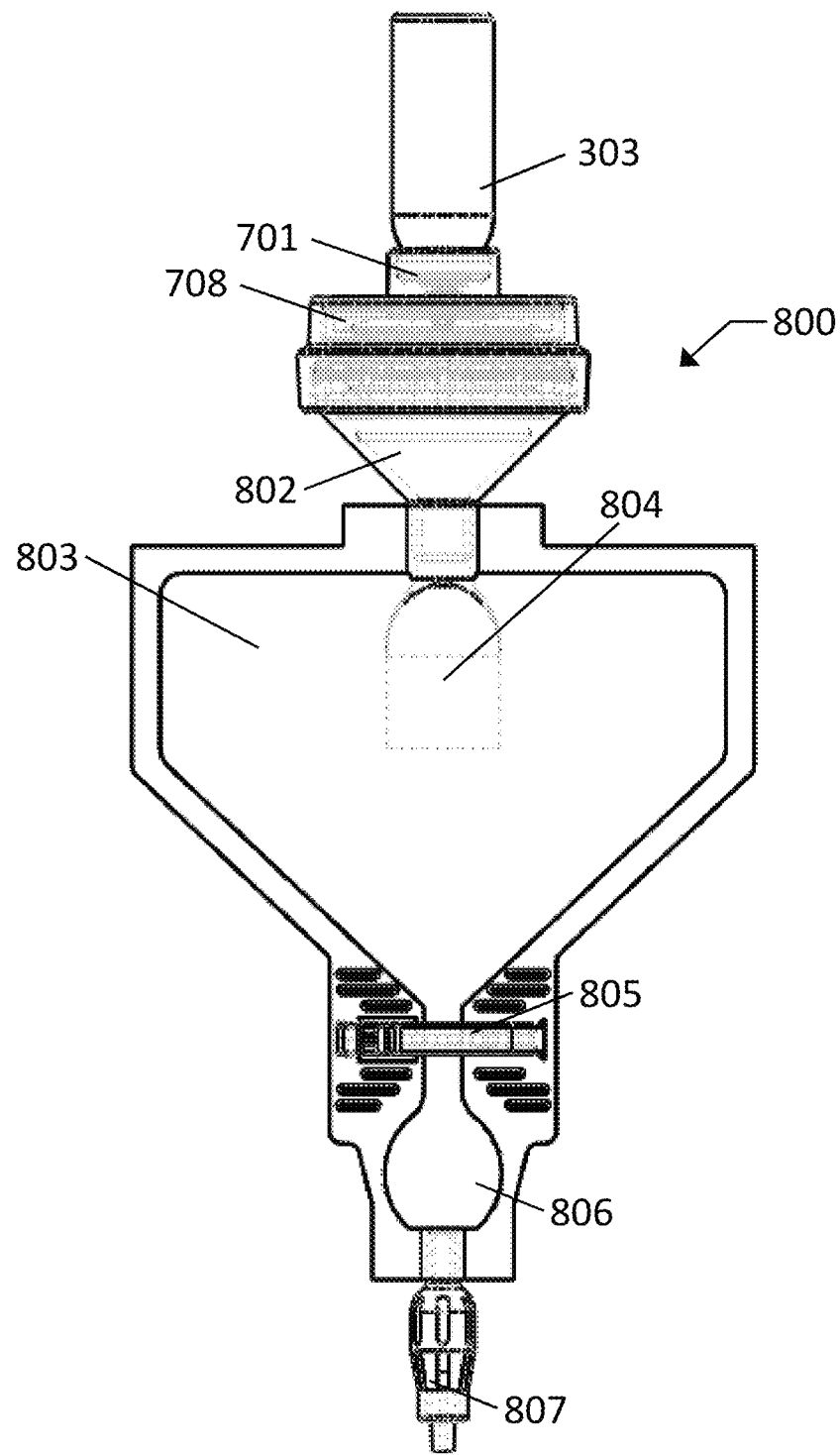
Figure 28:
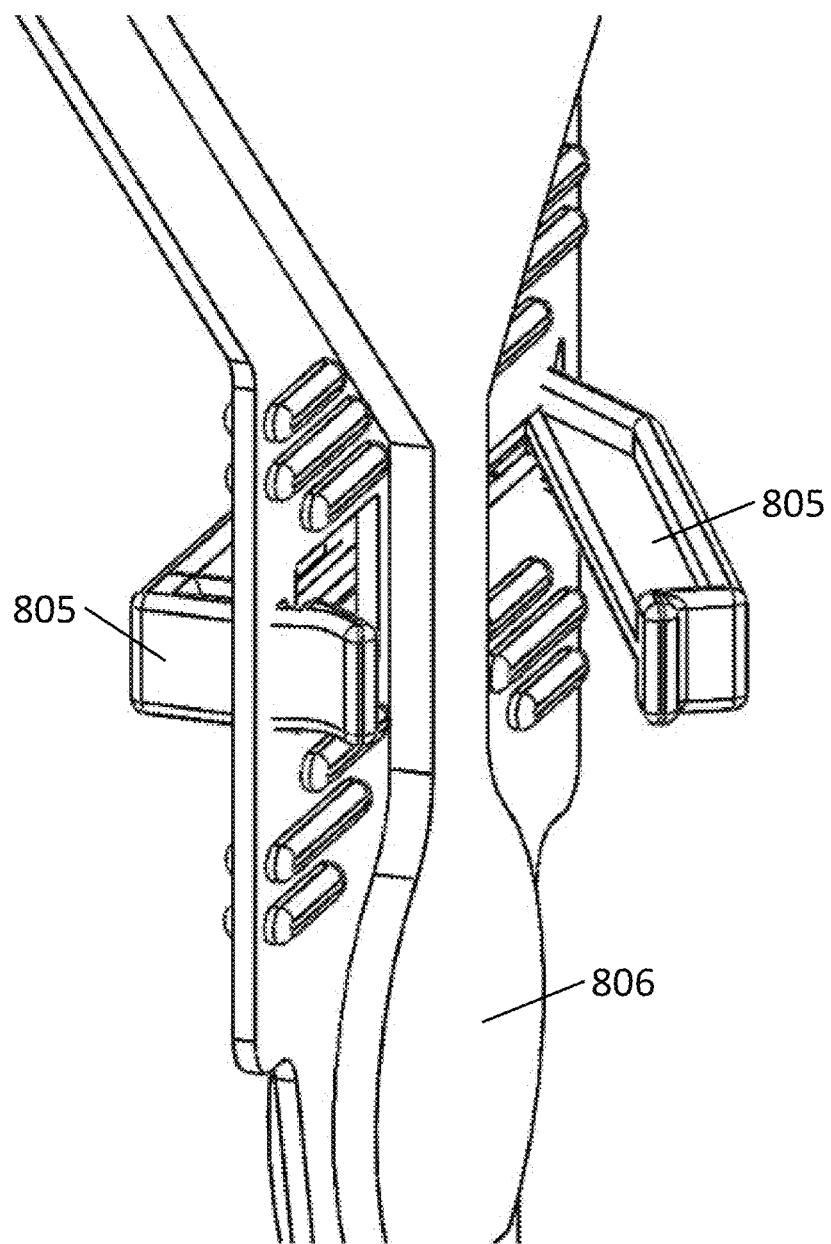

FIGS. 26 through 28 show an exemplary embodiment of a surface wipe collection and recovery device 800. Surface wipe material 707 is a non-woven, woven or open cell foam material with support 706 and attachment post 705. For collection of surface samples, a user holds onto attachment post 705 and support 706, or attaches attachment post 705 to elutor cap 701 and uses elutor cap 701 as a handle. A surface sample is then collected with the dry surface wipe material 707, or pre-wets the material or the surface with water, surfactant solution or other appropriate buffer solution. The surface sample is collected from an appropriate area and the attachment post is attached to elutor cap 701 (if not already attached). Elutor cap 701 and wipe material 707 are then inserted into elutor ring 708 and snapped into place with snap fit 712. When snapped into place, wipe material 707 becomes compressed as shown in 711 between elutor cap 701 and elutor ring 708. Compression of the wipe material 707 acts to keep elution foam from passing around the edge of the wipe material during the sample recovery process. The elutor ring 708 is then attached to sample bag adapter 802 with the two pieces sealed together at seal 801. The hand-held pressurized elution fluid canister 303 is then placed into fitting 702 and the user pushes down on the canister 303 to actuate valve stem 302 against valve stem port 703. Upon actuation, the valve stem 302 releases elution fluid which passes through flow splitter 704. Flow splitter 704 acts to push the elution fluid, which is rapidly turned into wet foam, away from the center flow path, so that it distributes evenly as it flows down and through the wipe material 707, recovering particles that were captured from the surface into the material. The foam is then dispensed through flat tube check valve 804 and into sample bag 803 and quickly breaks back down into a liquid sample. Because the bag 803 is flat and the system does not contain vents the bag 803 is inflated slightly as the wet foam is dispensed into the bag. Pinch valve 805 is then opened, if not already open, and the bag 803 is squeezed slightly to push fluid into the sample aliquot reservoir 806. The sample aliquot reservoir 806 can be custom configured to hold a set volume of sample for dispensing to assay cartridges or sample reservoirs. Pressure is then released from the bag 803 and the pinch valve 805 is closed. The user then attaches self-opening luer lock 807 to a separate assay cartridge or sample container and squeezes sample aliquot reservoir 806 to dispense the measured sample.

Figure 29:
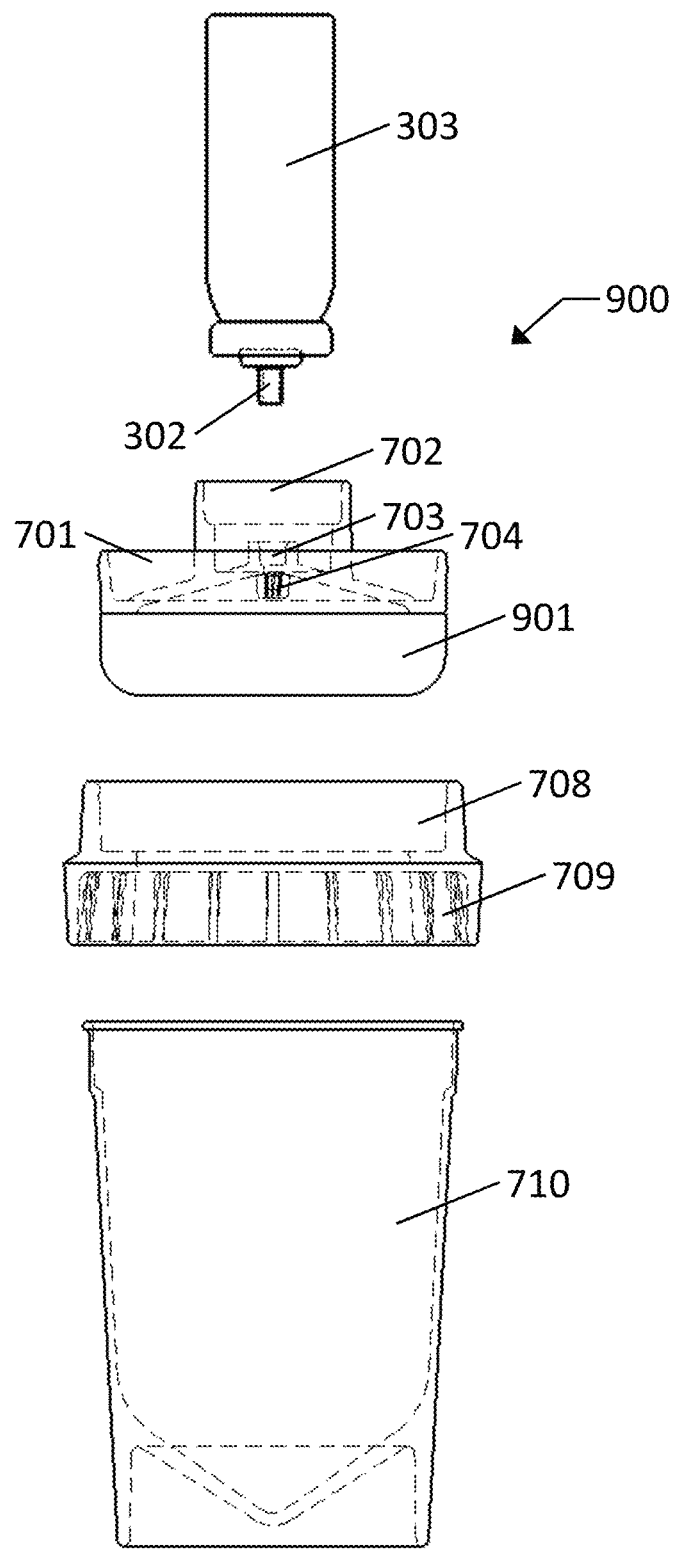
FIGS. 29 and 30 show an alternate configuration of a consumable surface wipe and elution device with a thick wipe material that is crushed around the edge to seal the material during the elution process, and a vented sample cup for catching the elution fluid, according to an exemplary embodiment of the present subject disclosure.
Figure 30:
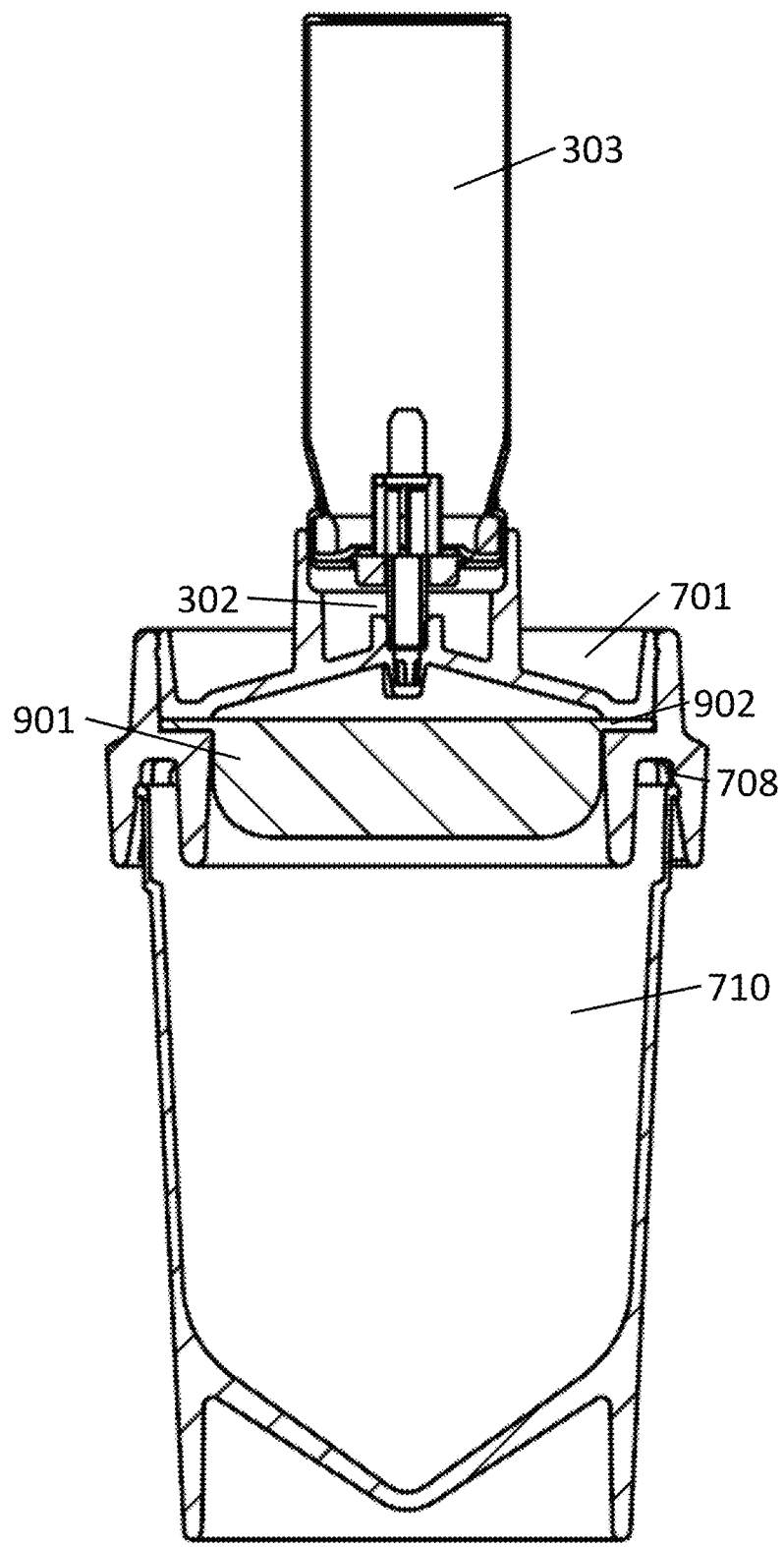

FIGS. 29 and 30 show an exemplary embodiment of surface wipe collection and recovery device 900. Surface wipe material 901 is a hydrophilic open cell foam material. For collection of surface samples, the elutor cap 701 is used as a handle. A surface sample is then collected with the dry surface wipe material 901, or the user pre-wets the material or the surface with water, surfactant solution or other appropriate buffer solution. The surface sample is collected from an appropriate area and the elutor cap 701 is inserted into elutor ring 708 and snapped into place with snap fit 712. When snapped into place, wipe material 901 becomes compressed as shown in 902 between elutor cap 701 and elutor ring 708. Compression of the wipe material 901 acts to keep elution foam from passing around the edge of the wipe material during the sample recovery process. The elutor ring 708 is then attached to sample cup 710. The hand-held pressurized elution fluid canister 303 is then placed into fitting 702 and the user pushes down on the canister 303 to actuate valve stem 302 against valve stem port 703. Upon actuation, the valve stem 302 releases elution fluid which passes through flow splitter 704. Flow splitter 704 acts to push the elution fluid, which is rapidly turned into wet foam away from the center flow path, so that it distributes evenly as it flows down and through the wipe material 901, recovering particles that were captured from the surface into the material. The foam is then dispensed into sample cup 710 and quickly breaks back down into a liquid sample. Gas vents 709 allow gas released from the wet foam to escape from the assembly, so that the entire assembly remains at or near to atmospheric pressure.

Figure 31:
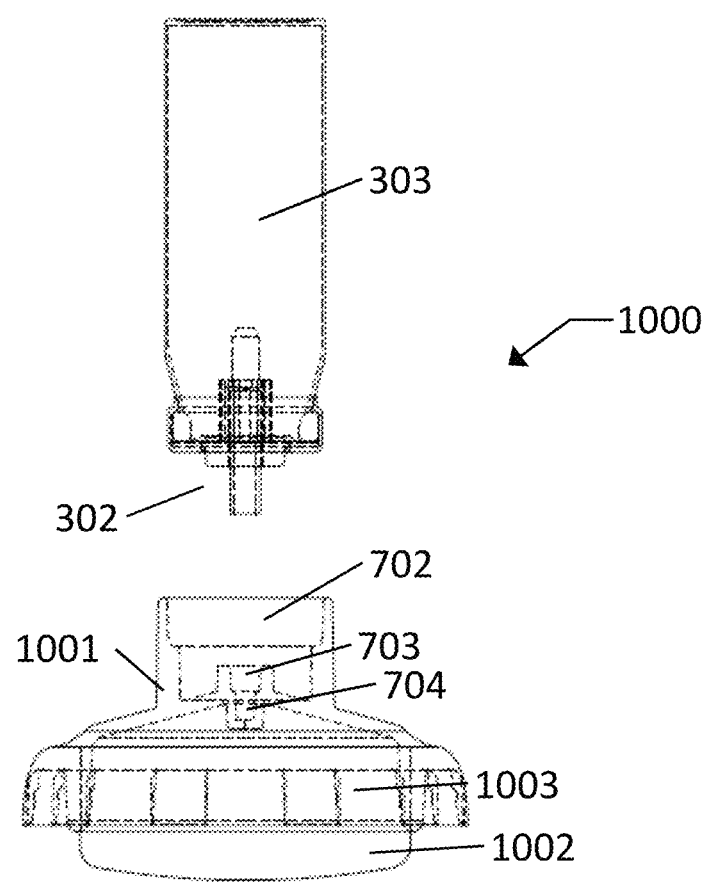
FIGS. 31 and 32 show an alternate configuration of a consumable surface wipe and elution device with a thick wipe material that is compressed and bonded at the edge to seal the material during the elution process, and a vented sample cup for catching the elution fluid, according to an exemplary embodiment of the present subject disclosure.
Figure 31:
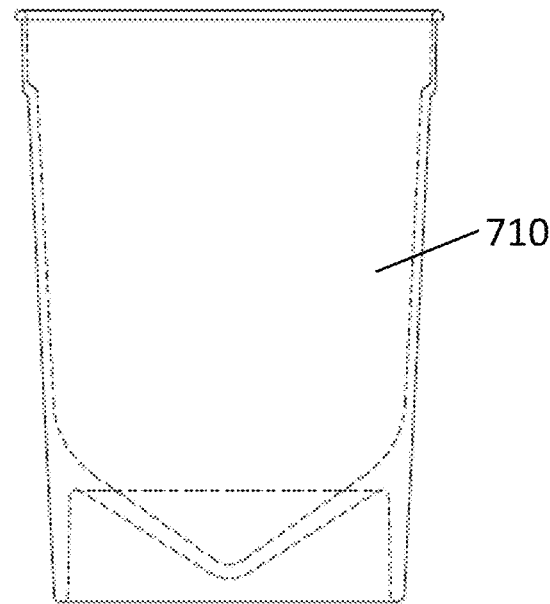
Figure 32:
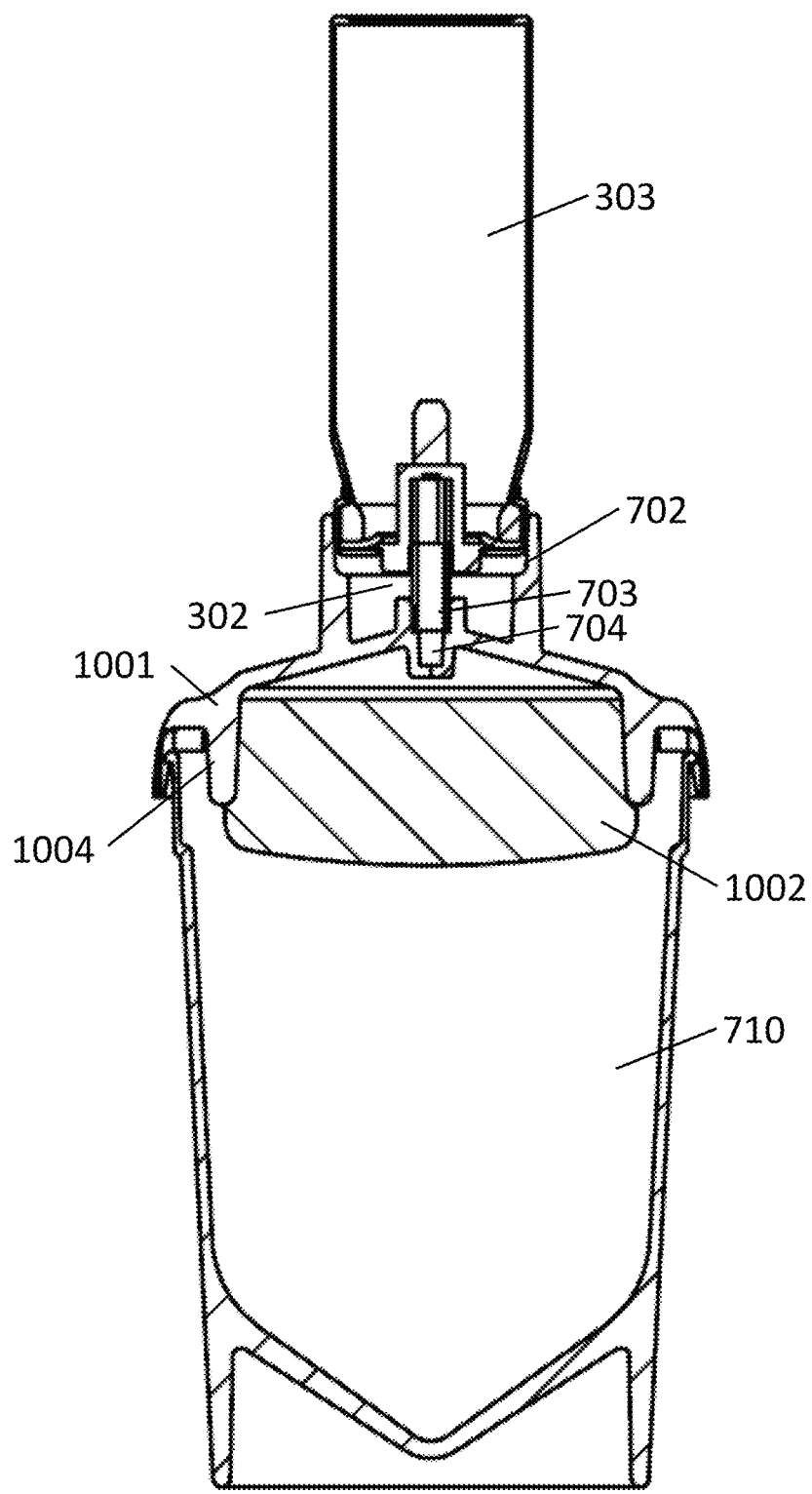

FIGS. 31 and 32 show an exemplary embodiment of a surface wipe collection and recovery device 1000. Surface wipe material 1002 is a hydrophilic open cell foam material. For collection of surface samples, the elutor cap/swab handle 1001 is used as a handle. The wipe material 1002 is bonded to the elutor cap/swab handle 1001 along surface 1004. The wipe material 1002 is cut slightly larger than the opening to ensure some compression of the wipe material and to reduce passage of foam along the bonding joint 1004. The bonding joint 1004 is also long enough so that the foam flow path is the same as at the bond location as at other locations in the wipe material. A surface sample is then collected with the dry surface wipe material 1002, or the user pre-wets the material or the surface with water, surfactant solution or other appropriate buffer solution. The surface sample is collected from an appropriate area and the elutor cap/swab handle 1001 is snapped onto sample cup 710. The hand-held pressurized elution fluid canister 303 is then placed into fitting 702 and the user pushes down on the canister 303 to actuate valve stem 302 against valve stem port 703. Upon actuation, the valve stem 302 releases elution fluid which passes through flow splitter 704. Flow splitter 704 acts to push the elution fluid, which is rapidly turned into a wet foam away from the center flow path, so that it distributes evenly as it flows down and through the wipe material 1002, recovering particles that were captured from the surface into the material. The foam is then dispensed into sample cup 710 and quickly breaks back down into a liquid sample. Gas vents 1003 allow gas released from the wet foam to escape from the assembly, so that the entire assembly remains at or near to atmospheric pressure.

Figure 33:
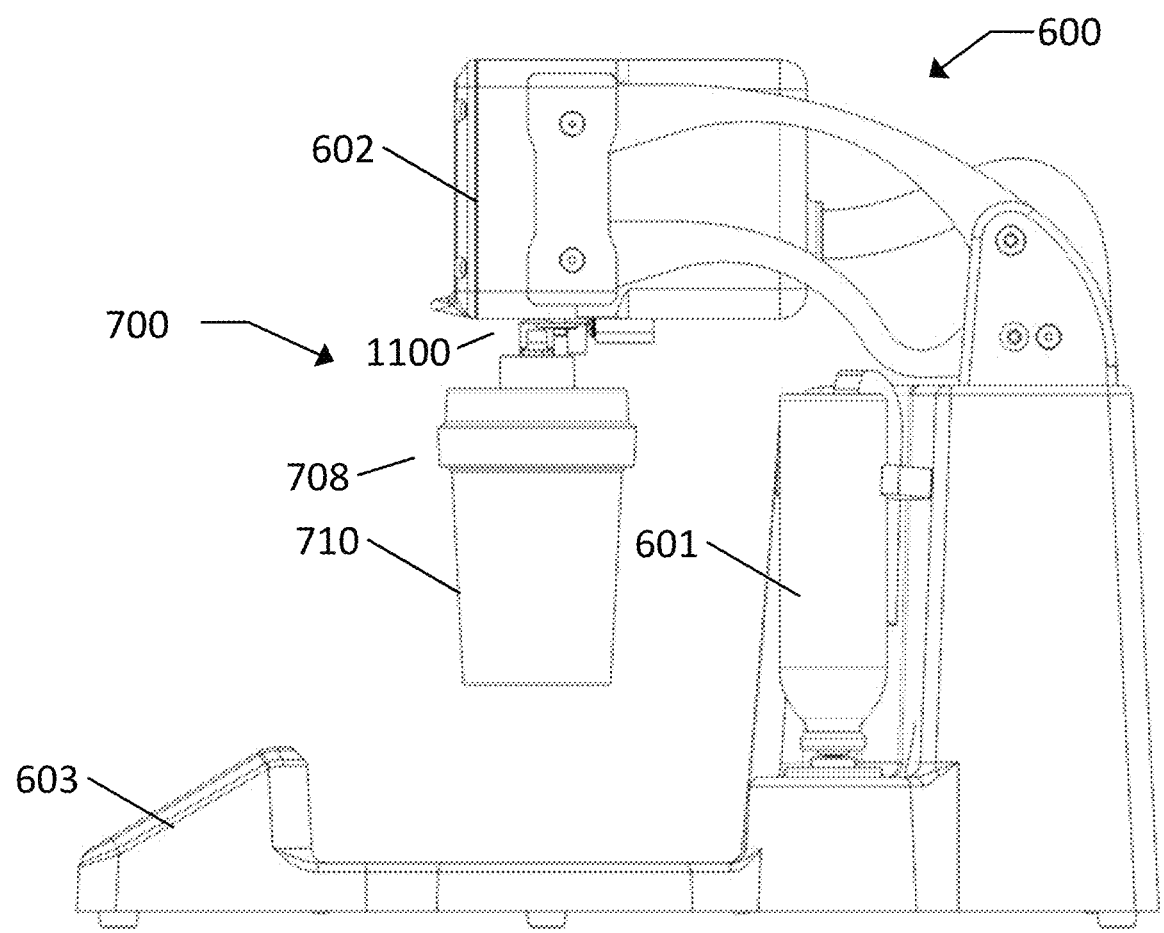
FIGS. 33 and 34 show an alternate configuration of a consumable surface wipe and elution device and various components with a thin wipe material and a vented sample cup for catching the elution fluid wherein the elution is performed by a flow of foam across the swab head using wet foam dispensed from Applicant's Concentrating Pipette Instrument, according to an exemplary embodiment of the present subject disclosure.
Figure 34:
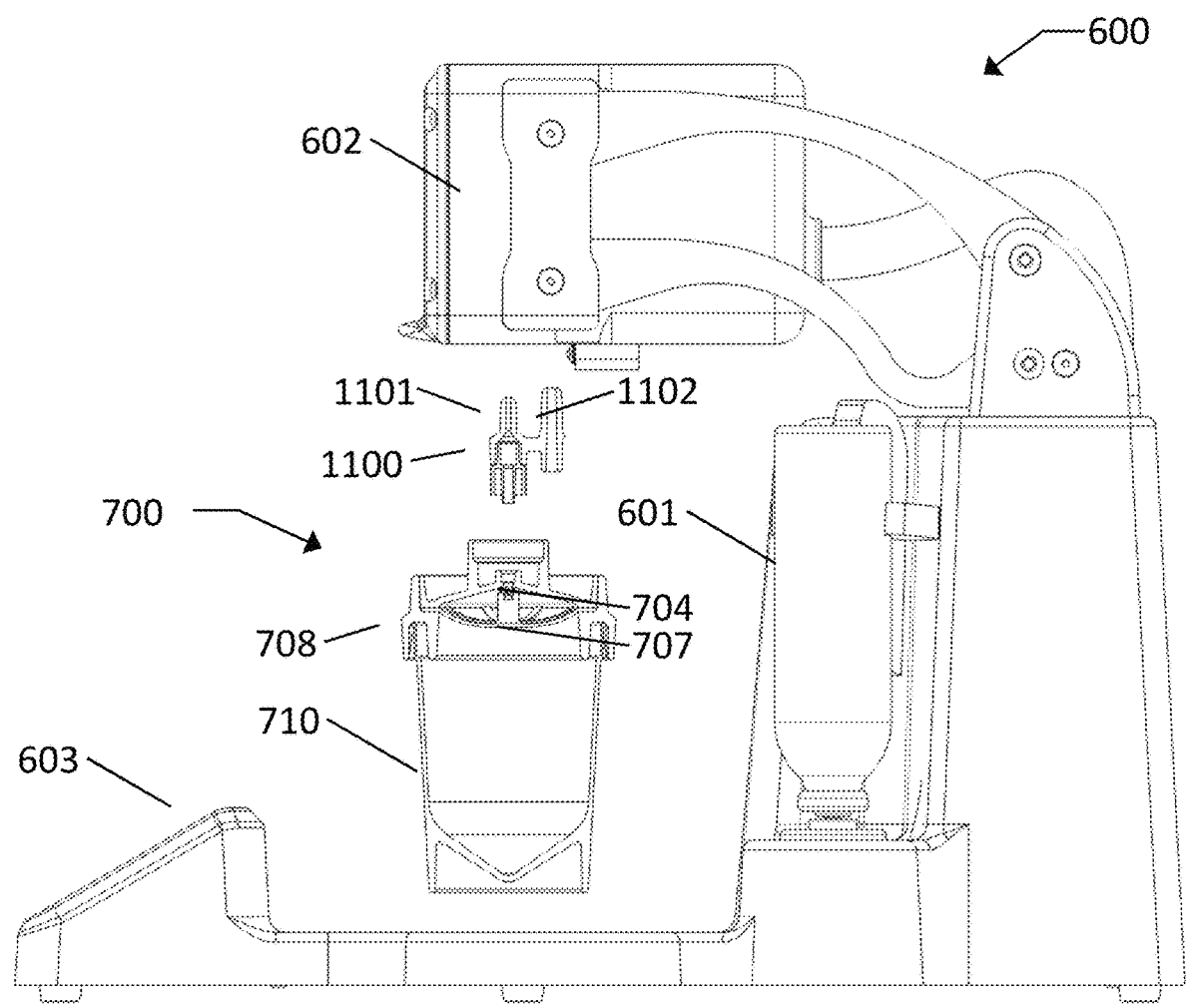

FIGS. 33 and 34 show an exemplary embodiment of a surface wipe collection and recovery device 700 for use with Applicant's Concentrating Pipette System 600. After collection of a surface sample with surface wipe material 707, the two nipples 1101 and 1102 on the fitting 1100 are inserted into the Concentrating Pipette 600 head 602. After insertion, the user interface 603 is used to set the elution fluid setpoints to allow the appropriate volume of elution fluid to be dispensed and an elution is performed. Elution fluid is released by an electromechanical elution fluid valve within the Concentrating Pipette 600 from the pressurized elution fluid canister 601. Elution fluid is released in the form of wet foam which passes through elution fluid nipple 1101, fittings 1100 and flow splitter 704. Flow splitter 704 acts to push the elution fluid, which is rapidly turned into wet foam away from the center flow path, so that it distributes evenly as it flows down and through the wipe material 707, recovering particles that were captured from the surface into the material. The foam is then dispensed into sample cup 710 and quickly breaks back down into a liquid sample. Gas vents 709 allow gas released from the wet foam to escape from the assembly, so that the entire assembly remains at or near to atmospheric pressure.

It is desirable to be able to efficiently collect and elute dry deposited and wet deposited and then dried materials, and also to be able to absorb still wet materials and to be able to captured powder type materials. As would be apparent to a person skilled in the art, a number of types of materials may be used as the collection material in the disclosed systems. Hydrophilic surface sampling materials are desired for collection of dried-on material, liquid samples, and powders from smooth surfaces. These may include materials such as flocked materials, rayon, cellulose and cotton materials and many others that will be apparent to someone skilled in the art. Electret surface sampling materials, flocked materials and other hydrophobic or hydrophilic materials may be used for collection of dry, aerosol deposited materials or dry, dispersed powders from smooth surfaces. Sponge materials and durable wipe materials with thick fibrous surfaces may be used for collection from rougher and abrasive surfaces.

It will be appreciated that the foregoing instrumentalities teach by way of example, and not by limitation. Accordingly, those skilled in the art understand that the subject matter is not limited to what is strictly disclosed, but also pertains to what is understood by those skilled in the art on the basis of the teachings herein. The inventors hereby state their subject matter to rely, as may be needed, upon the Doctrine of Equivalents to protect the fullness of their rights in what is claimed.

What is claimed is:

1. A portable system for collecting and extracting a sample from a surface, the system comprising:
 a swab having a head at one end of an extended shaft, the extended shaft having a lumen that extends substantially throughout the length of the shaft;
 a portable canister having a valve stem and containing pressurized wet foam;
 a cradle for housing the canister;
 a canister valve actuator connected to the cradle;
 a dispensing lever connected to the canister valve actuator;
 wherein upon pressing of the dispensing lever, the canister valve actuator presses on the valve stem on the pressurized canister;
 wherein as the pressurized foam is introduced at an opposite end of the extended shaft with respect to the head, the wet foam travels through the lumen and elutes samples from the head.

2. The system in claim 1, wherein the extended shaft includes apertures near the head to allow for uniform distribution of wet foam through the head and onto its exterior surface.

3. The system in claim 2, wherein the apertures comprise a porous section of the shaft within the head.

4. The system in claim 1, further comprising a collection receptacle for collecting the wet foam with sample after elution from the swab head.

5. The system in claim 1, further comprising a swab fitting which connects the valve stem to an end of the extended shaft opposite of the head.

6. The system in claim 1, wherein the swab is used to collect particles, dried-on materials, or liquid samples from a surface prior to attaching to the portable canister valve stem and being eluted.

7. The system in claim 1, wherein the swab is attached to the valve stem and held in place while the cradle is grasped by a user while sampling a surface.

8. The system in claim 7, wherein a volume of foam is dispensed prior to or during collection to enable collection from a surface using a wet swab head.

9. The system in claim 1, wherein the canister contains water with a surfactant, a buffer, and a water soluble gas.

10. The system in claim 9, wherein the surfactant is made up of one or more of Tween 20, Tween 80, Triton X-100, sodium dodecyl sulfate, or other ionic, nonionic, cationic, zwitterionic, or proteins.

11. The system in claim 9, wherein the soluble gas is made up of one or more of carbon dioxide, nitrous oxide, or nitrogen.

12. The system in claim 1, further comprising an orifice within the canister valve stem to control the flow of the liquid exiting the canister.

13. The system in claim 1, further comprising an electro-mechanical valve to control a volume of foam dispensed.

14. The system in claim 1, further comprising a mechanical valve system to control a volume of foam dispensed.

* * * * *